US012564152B2

(12) United States Patent
Morton et al.

(10) Patent No.: US 12,564,152 B2
(45) Date of Patent: Mar. 3, 2026

(54) SYSTEM AND METHOD FOR MANAGEMENT OF SENSOR DATA BASED ON HIGH-VALUE DATA MODEL

(71) Applicant: Dell Products, LP, Round Rock, TX (US)

(72) Inventors: Michael J. Morton, Morrisville, NC (US); Steve J. Todd, Center Conway, NH (US); Richard A. Backhouse, Apex, NC (US)

(73) Assignee: BOOMI, LP, Chesterbrook, PA (US)

( * ) Notice: Subject to any disclaimer, the term of this patent is extended or adjusted under 35 U.S.C. 154(b) by 258 days.

(21) Appl. No.: 16/530,909

(22) Filed: Aug. 2, 2019

(65) Prior Publication Data

US 2021/0035124 A1 Feb. 4, 2021

(51) Int. Cl.
G06F 16/00 (2019.01)
A01H 6/36 (2018.01)

(52) U.S. Cl.
CPC ............. *A01H 6/368* (2018.05); *G06F 16/00* (2019.01)

(58) Field of Classification Search
CPC ............................... A01H 6/368; G06F 16/00
USPC ..................................................... 705/7.29, 7
See application file for complete search history.

(56) References Cited

U.S. PATENT DOCUMENTS 10,050,978 B2    8/2018  Morton
10,324,962 B1    6/2019  Todd 2006/0259217 A1*  11/2006  Gorinevsky ....... G05B 23/0213
                                                              702/184
2011/0074587 A1*   3/2011  Hamm ................... G06Q 10/08
                                                              340/584
2017/0303846 A1*  10/2017  O'Brien ................ A61B 5/486

OTHER PUBLICATIONS

Wirawan, I Made, IoT Communication System using Publish-subscribe, 2018, 2018 International Seminar on Application for Technology of Information and Communication, Iniversitas Negeri Malang, p. 61-65 (Year: 2018).*

* cited by examiner

*Primary Examiner* — Stephen S Hong
*Assistant Examiner* — Tionna M Burke
(74) *Attorney, Agent, or Firm* — Prol Intellectual Property Law, PLLC; H. Kenneth Prol

(57) ABSTRACT

A method of integrating high-value sensor data may comprise receiving a sensor reading from an Internet of Things (IoT) sensor, via a gateway network interface device in an enterprise network, receiving a high-value data model including a model field value matching a metadata descriptor associated with the sensor reading, and a valuation score associated with a business use case, and receiving a data access catalog associating the business use case with a client of the enterprise network who is not subscribed to receive the sensor reading. The method may further include identifying the client as a recommended recipient, and transmitting the sensor reading to the recommended recipient if the valuation score associated with the business use case within the high-value data model meets a high-value data threshold value.

20 Claims, 8 Drawing Sheets

SYSTEM AND METHOD FOR MANAGEMENT OF SENSOR DATA BASED ON HIGH-VALUE DATA MODEL

FIELD OF THE DISCLOSURE

The present disclosure relates generally to management of sensor data at one or more gateways in a network. More specifically, the present disclosure relates to an improved process for identifying high-value sensor data across a plurality of gateways or clients, and automatic processing of such identified high-value sensor data for delivery to users.

BACKGROUND

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

For purposes of this disclosure, an information handling system may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, an information handling system may be a personal computer (e.g., desktop or laptop), tablet computer, mobile device (e.g., personal digital assistant (PDA) or smart phone), a head-mounted display device, server (e.g., blade server or rack server), a network storage device, a network storage device, a gateway device, and edge gateway device, a switch router or other network communication device, other consumer electronic devices, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communicating with external devices as well as various input and output (I/O) devices, such as a keyboard, a mouse, touchscreen and/or a video display. The information handling system may also include one or more buses operable to transmit communications between the various hardware components. Further, the information handling system may include telecommunication, network communication, and video communication capabilities and require communication among a variety of data formats or sensor devices.

BRIEF DESCRIPTION OF THE DRAWINGS

The present disclosure will now be described by way of example with reference to the following drawings in which.

The use of the same reference symbols in different drawings may indicate similar or identical items.

DETAILED DESCRIPTION

Figure 1:
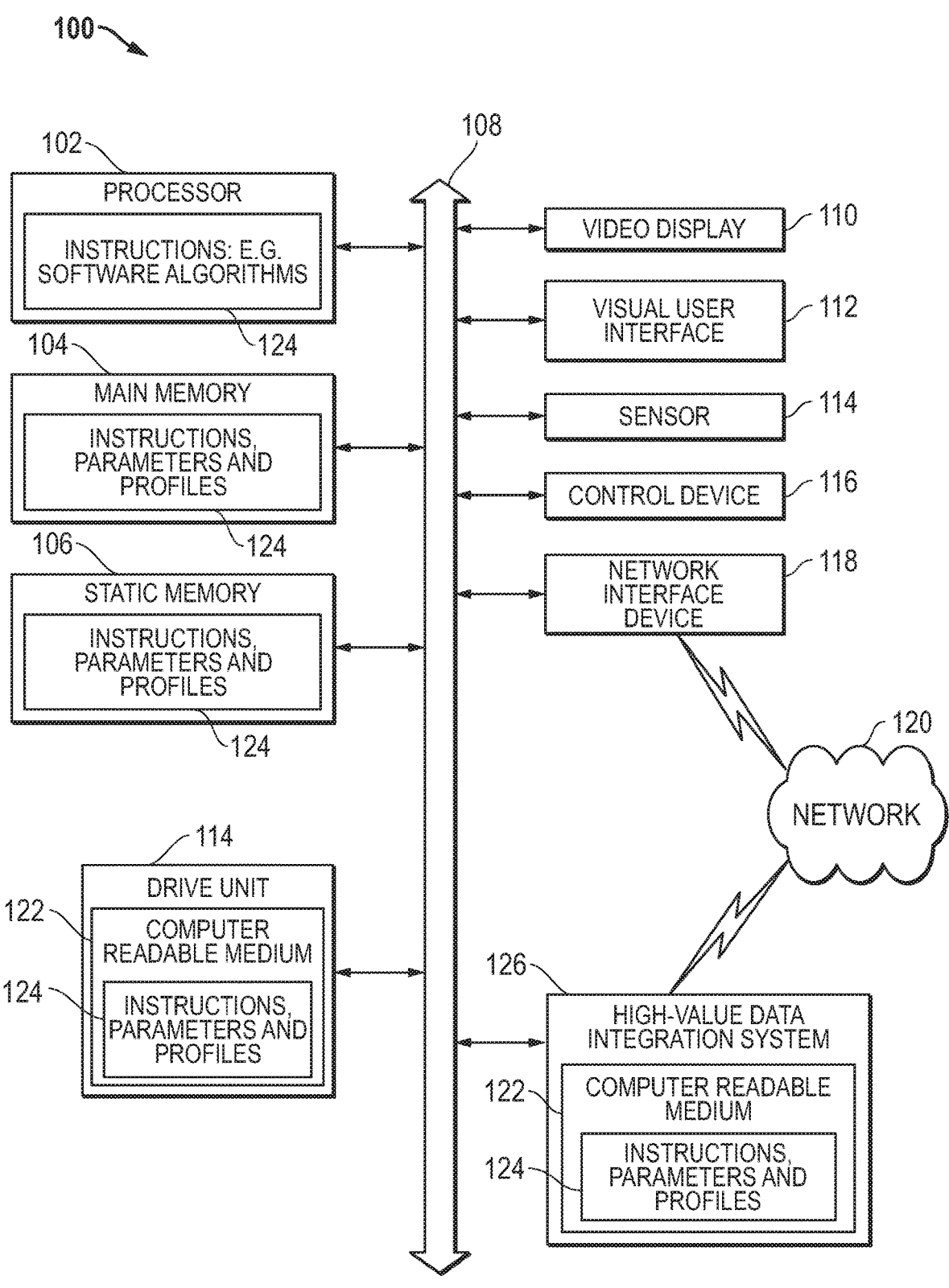
FIG. 1 is a block diagram illustrating an information handling system according to an embodiment of the present disclosure.

The following description in combination with the Figures is provided to assist in understanding the teachings disclosed herein. The description is focused on specific implementations and embodiments of the teachings, and is provided to assist in describing the teachings. This focus should not be interpreted as a limitation on the scope or applicability of the teachings.

Today, most corporations or other enterprises have sophisticated computing systems that are used both for internal operations, and for communicating outside the enterprise's network. Much of present day information exchange is conducted electronically, via communications networks, both internally to the enterprise, and among enterprises. Enterprises or other entities typically have a large information technology (IT) infrastructure comprising a network of computing resources distributed across a geographic environment. These computing resources may be mobile (e.g., in a vehicle or mobile device) or remain at a fixed location (e.g., in stationary equipment). In some scenarios, these computing resources are part of an Internet of Things (IoT) network. For example, a given IoT network may include sensors that monitor one or more conditions in one or more environments in which they reside by collecting data and providing data (either raw collected data and/or data processed by the sensor) to one or more computing nodes, i.e., gateways, associated with the enterprise or other entity. By way of example only, such sensors may be part of smart devices, smart cities, smart grids, connected cars, health monitors, home automation and energy management systems, and remote industrial process control systems, just to name a few applications.

It is often desirable or necessary to exchange information/ data between distinctly different computing systems, computer networks, software applications, etc. The enabling of communications between diverse systems/networks/applications in connection with the conducting of business processes is often referred to as "business process integration." In the business process integration context, there is a significant need to aggregate or integrate various types of sensor data at one or more locations within an enterprise network for analysis or notification of an event occurrence. In many scenarios, data continuously streams in from sensors in an IoT network. However, the ability to effectively process and leverage such sensor data presents significant challenges to the enterprise or entity.

In order to efficiently manage such sensor data, it may be beneficial to devote more resources to the processing and storage of higher value sensor data, rather than sensor data that is rarely used or leveraged by subscribing clients. In existing systems, the valuation of the data coming from any particular sensor (or group of sensors) at the point of ingest is typically unknown. Even in systems where the valuation of sensor data is known, management of the data processing and storage is not optimized based on these valuations. Such mismanagement of resources may result in several types of inefficiencies. For example, high-value sensor data may be under-distributed, due to constrained or limited resources to perform processing, storage, and delivery of such high-value data. This may be due, in part, to another potential inefficiency—over-distribution of low-value data. Other issues associated with integrating sensor data regardless of data valuation may include errors in transformation of data between endpoints, and failure to secure high-value data or the sensors consistently generating such high-value. A system that more efficiently processes and distributes sensor data, based on a valuation of that data is needed.

The high-value data integration system in embodiments of the present disclosure may address these issues by identifying high-value data, building a model to describe such data, and automatically developing application programming interfaces (APIs) that can automatically locate and distribute such high-value data or other sensor data similar to the identified high-value data. In embodiments of the present disclosure, the high-value data integration system may identify high-value data by analyzing metadata associated with sensor readings that includes previously determined valuation scores for the sensor readings, or by monitoring requests from third-party APIs mining for high-value data, and flagging sensor readings responsive to those queries as high-value. Once a high-value sensor reading is identified in an embodiment, a high-value data model may be created to describe the high-value sensor reading. Such a high-value data model may include information such as an identification of the individual sensor generating the data, the type of sensor (e.g., thermostat or motor), the firmware and version operating at the sensor, the reason a third-party API or a subscribing user has requested the data in the past, whether the reading is shareable, any application or user access restrictions (e.g. encryption, password-authentication, access restrictions based on route of access) that apply, the value of the reading, or the gateway at which the sensor reading was collected and processed for delivery to a subscribing end user. The high-value data models in embodiments may be generated for each sensor reading identified as high-value, and may be stored in a high-value data model control center, which may reside on-site within the enterprise network, or may be cloud-based.

The high-value data model control center in embodiments may also operate at least a portion of the high-value data integration system to create a retrieval API capable of retrieving other sensor data described by one or more fields of a stored high-value data model. For example, a stored high-value data model may describe a high-value sensor reading from a first thermostat measuring relative humidity in communication with a first gateway. The retrieval API may then be deployed at a first or second gateway to gather, process, and publish relative humidity sensor readings from the first thermostat or other thermostats in communication with the first or second gateways. In another example, the high-value data integration system may monitor a request from a third party API to determine the firmware version that is currently operating on each of a plurality of motors for the purpose of identifying a malfunctioning device. The high-value data integration system in such an embodiment may create a high-value data model for each response to the API request, identifying one of a plurality of motors and each of their respective firmware versions. Each of these high-value data models created in embodiments may also identify the stated purpose of identifying a malfunctioning device. Once such a high-value data model is created, the high-value data integration system in embodiments may automatically create a retrieval API, for execution at any gateway, that may automatically retrieve, process, and deliver the identities of a plurality of motors (or other IoT device types), and their current firmware versions to any client subscribing to data for the purpose of identifying malfunctioning devices. In such a way, the high-value data integration system in embodiments may leverage knowledge of which data is of high valuation to more efficiently process, store, and distribute sensor readings across networks.

Retrieval APIs in embodiments described herein may be automatically created by customizing generic integration processes using field values within high-value data models. Generic integration processes in embodiments described herein may be created to comply with the vendor-agnostic open source EdgeX Foundry™ platform architecture developed by the Linux Foundation. The EdgeX Foundry™ platform architecture provides a framework for processing of sensor data within a gateway device. Among the benefits of EdgeX Foundry™ platform architecture is a streamlined distribution method that allows for filtering of incoming sensor data based on client subscriptions registered via a third-party Representational State Transfer (REST) API. Using the framework outlined by the EdgeX Foundry™ platform architecture, a retrieval API may be created that filters through sensor data persisting at a gateway to identify sensor data requested by a specific subscribing client, and publishing that filtered data directly to the client. Client subscriptions in existing EdgeX Foundry™ platform architectures may request sensor data from a type of IoT sensor (e.g., thermostat), a specific IoT device (e.g., identified by MAC address), or by a type of sensor reading taken by the device (e.g., temperature, but not humidity). This EdgeX Foundry™ platform architecture allows for the filtering of data prior to publication to the client, or prior to delivery of sensor data to a data lake, but does not filter outgoing sensor data based on valuation of the sensor data. Thus, processing of sensor data at a gateway using the EdgeX Foundry™ platform architecture may still result in the inefficiencies associated with over publication of low-value data, under publication of high-value data, and unnecessary processing (e.g., filtering and transforming for publication) of low-value data.

Embodiments of the present disclosure improve upon the EdgeX Foundry™ platform architecture by creating a retrieval API that conforms with the EdgeX Foundry™ platform architecture, while also leveraging valuation scores for incoming sensor data using one or more fields of the high-value data models described herein. The EdgeX Foundry™ platform architecture includes several services, including core services, where core data and metadata for sensor data are persisted, and export services, where client registration and distributions microservices are persisted. The distribution microservices within the EdgeX Foundry™ platform architecture may filter and transform data based on client subscriptions maintained by the client registration microservice prior to publication to subscribing clients. The retrieval API described in embodiments herein may allow subscribing clients to request sensor data by sensor type, sensor ID, and field value, as outlined within the EdgeX Foundry™ platform architecture.

As sensor readings are received from the core services layer at the export services layer, the distribution microservices in the EdgeX Foundry™ platform architecture may filter and transform data for publication to a subscribing client based on the subscriptions maintained by the enhanced client registration microservices of the retrieval API. In the existing EdgeX Foundry™ platform architecture, the distribution microservices may receive sensor data (including the sensor readings and associated metadata) from the core services layer, and analyze the sensor data to identify the type of sensor that generated the data, the identity of the specific sensor that generated the data, and a field value within the sensor data. The distribution microservices in existing systems may then cross-reference this information with client registrations maintained with the client registration microservices to identify one or more clients subscribing to receive such sensor data, as described by a client-specified sensor type, sensor ID, or field value stored in a client registration record.

As such sensor readings are published to subscribing clients, or transmitted to clients pursuant to data-mining API calls, the high-value data integration system in embodiments may create one or more high-value data models describing such sensor readings. High-value data models in embodiments may associate a subscribing client with one or more descriptors of the published sensor reading found in the contents of the published sensor reading or its attached metadata (e.g., type of sensor generating the sensor, ID of the originating sensor, type of reading performed, gateway at which the reading was received, or version of firmware operating at originating sensor). A valuation score describing the usefulness of the published sensor reading in executing one or more business uses (e.g., identifying a malfunctioning IoT sensor) may also be associated with the published sensor reading and metadata in an embodiment. Such valuation score(s) may also be included in the high-value data models. As new sensor readings are imported into gateways within the enterprise network, these high-value data models may be used to gauge the usefulness of these new sensor readings in similar business use cases. This may allow for reallocation of resources away from new sensor readings determined, through analysis of the high-value data models, to be of low-value, and toward new sensors readings determined to be of high-value.

The retrieval API in embodiments described herein improves upon the classic approach of the EdgeX Foundry™ platform architecture by further identifying recommended clients that may not be subscribed to the new incoming sensor readings, but would likely find the data to be of high-value. For example, in the enhanced client registration microservices of the retrieval API, one or more existing high-value data models describing the new sensor data may be identified. One or more of these high-value data models in embodiments may associate the newly received sensor readings with a valuation score for a given or preset business use. The retrieval API in embodiments described herein may leverage this valuation by identifying one or more recommended clients who are not subscribed to receive the newly received sensor reading, but who have used similar previous sensor readings for the same business purpose identified in the high-value data model. In other words, the retrieval API may identify recommended clients that have not subscribed to the incoming data, but who may nevertheless find the incoming sensor data to be of a high-value for a specific purpose. By publishing such sensor data to the recommended client, along with an indication that such sensor data is being published for the specifically identified purpose, the retrieval API in embodiments described herein may overcome the inefficiency of under-publication of high-value data.

Because the retrieval API described herein allows for clients to request firmware operating on a sensor, and sensor data of a specific valuation score, and to describe the purpose for the subscription to certain sensor data, the distribution microservices of the retrieval API described herein may improve upon the existing EdgeX Foundry™ platform architecture by providing enhanced filtering abilities. For example, the retrieval API described herein may immediately filter out any low-value sensor data incoming from the core services, as defined by the valuation score specified by the client in the enhanced retrieval API client registration microservices. In such a way, the retrieval API may avoid unnecessary processing (e.g., filtering and transformation of data for publication) of low-value data.

The high-value data integration system in embodiments herein may automatically generate APIs capable of distributing sensor data described in a high value data model to clients subscribed to receive such data or similar data. Such a retrieval API may be created in an embodiment by customizing a template EdgeX Foundry™ platform architecture to distribute only sensor readings identified as high-value based on descriptions given within a high-value data model. For example, a template EdgeX Foundry™ platform architecture may be created by creating container code sets directing functionality of each EdgeX Foundry™ microservice. Such container code sets in an EdgeX Foundry™ platform architecture may operate to direct gathering, filtering, and distribution of sensor data to clients based on parameter values. The high-value data integration system in embodiments described herein may customize template EdgeX Foundry™ platform architectures, and thus create retrieval APIs as described herein, by creating specific parameter values corresponding to data descriptions stored in high-value data models. Upon execution of such tailored parameter values, the container code sets incorporated from the template EdgeX Foundry™ platform architecture may filter and distribute only sensor data having a high-value to the receiving clients. In such a way, embodiments of the present disclosure allow for automatic generation and updating of retrieval APIs operating according to the EdgeX Foundry™ platform architecture that reduce over-publication of low-value sensor data and under-publication of high-value data.

FIG. 1 is a block diagram illustrating an information handling system, according to an embodiment of the present disclosure. Information handling system 100 can include processing resources for executing machine-executable code, such as a central processing unit (CPU), a programmable logic array (PLA), an embedded device such as a System-on-a-Chip (SoC), or other control logic hardware used in an information handling system several examples of which are described herein. Information handling system 100 can also include one or more computer-readable media for storing machine-executable code, such as software or data. Additional components of information handling system 100 can include one or more storage devices that can store machine-executable code, one or more communications ports for communicating with external devices, and various input and output (I/O) devices, such as a keyboard, a mouse, and a video display. Information handling system 100 can also include one or more buses operable to transmit information between the various hardware components.

FIG. 1 illustrates an information handling system 100 similar to information handling systems according to several aspects of the present disclosure. For example, an information handling system 100 may be any mobile or other computing device capable of executing a set of instructions (sequential or otherwise) that specify actions to be taken by that machine. In a particular embodiment, the information handling system 100 can be implemented using electronic devices that provide voice, video, or data communication. Further, while a single information handling system 100 is illustrated, the term "system" shall also be taken to include any collection of systems or sub-systems that individually or jointly execute a set, or multiple sets, of instructions to perform one or more computer functions.

Information handling system 100 can include devices or modules that embody one or more of the devices or execute instructions for the one or more systems and modules herein, and operates to perform one or more of the methods. The information handling system 100 may execute code 124 for the high-value data integration system 126 that may operate on servers or systems, remote data centers, gateway network devices such as a gateway computing node, or on-box in individual client information handling systems such as a local display device, or a remote display device, according to various embodiments herein. In some embodiments, it is understood any or all portions of code 124 for the high-value data integration system 126 may operate on a plurality of information handling systems 100.

The information handling system 100 may include a processor 102 such as a central processing unit (CPU), a graphics-processing unit (GPU), control logic or some combination of the same. Any of the processing resources may operate to execute code that is either firmware or software code. Moreover, the information handling system 100 can include memory such as main memory 104, static memory 106, drive unit 114, or the computer readable medium 122 of the high-value data integration system 126 (volatile (e.g. random-access memory, etc.), nonvolatile (read-only memory, flash memory etc.) or any combination thereof). Additional components of the information handling system can include one or more storage devices such as static memory 106, drive unit 114, and the computer readable medium 122 of the high-value data integration system 126. The information handling system 100 can also include one or more buses 108 operable to transmit communications between the various hardware components such as any combination of various input and output (I/O) devices.

Portions of an information handling system may themselves be considered information handling systems.

As shown, the information handling system 100 may further include a video display 110, such as a liquid crystal display (LCD), an organic light emitting diode (OLED), a flat panel display, a solid state display, or other display device. Additionally, the information handling system 100 may include a control device 116, such as an alpha numeric control device, a keyboard, a mouse, touchpad, fingerprint scanner, retinal scanner, face recognition device, voice recognition device, or gesture or touch screen input.

The information handling system 100 may further include a visual user interface 112. The visual user interface 112 in an embodiment may provide a visual designer environment permitting a user to define process flows between applications/systems, such as between gateway network devices and IoT sensor devices, and to model a customized integration process.

The information handling system 100 can represent a server device whose resources can be shared by multiple client devices, or it can represent an individual client device, such as a desktop personal computer, a laptop computer, a tablet computer, or a mobile phone. In a networked deployment, the information handling system 100 may operate in the capacity of a server or as a client user computer in a server-client user network environment, or as a peer computer system in a peer-to-peer (or distributed) network environment.

The information handling system 100 can include a set of instructions 124 that can be executed to cause the computer system to perform any one or more of the methods or computer based functions disclosed herein. For example, information handling system 100 includes one or more application programs 124, and Basic Input/Output System and Firmware (BIOS/FW) code 124. BIOS/FW code 124 functions to initialize information handling system 100 on power up, to launch an operating system, and to manage input and output interactions between the operating system and the other elements of information handling system 100. In a particular embodiment, BIOS/FW code 124 reside in memory 104, and include machine-executable code that is executed by processor 102 to perform various functions of information handling system 100. In another embodiment (not illustrated), application programs and BIOS/FW code reside in another storage medium of information handling system 100. For example, application programs and BIOS/FW code can reside in static memory 106, drive 114, in a ROM (not illustrated) associated with information handling system 100 or other memory. Other options include application programs and BIOS/FW code sourced from remote locations, for example via a hypervisor or other system, that may be associated with various devices of information handling system 100 partially in memory 104, storage system 106, drive unit 114 or in a storage system (not illustrated) associated with network interface device 118 or any combination thereof. Network interface device 118 is a structure in information handling system 100 for establishing network connectivity to a network 120 to transmit or receive data for information handling system 100. Application programs 124, and BIOS/FW code 124 can each be implemented as single programs, or as separate programs carrying out the various features as described herein. Application program interfaces (APIs) such as WinAPIs (e.g. Win32, Win32s, Win64, and WinCE), or APIs generated using open source technology such as EdgeX FoundryIM, Swaggerℒ, OpenAPI Generatorℒ, ReDocE, LucyBot Doc-Gent, API TransformerE, DapperDoxE, Widdershinsℒ, and

9

10

API SpecConverterĿ may enable application programs 124 to interact or integrate operations with one another. For example, an API located remotely from the information handling system 100 in some embodiments may operate to transmit and receive notifications and instructions between the remote location and the high-value data integration system 126.

In an example of the present disclosure, instructions 124 may execute software for generating an API for execution of an integration process involving data transfer or manipulation between an enterprise system/network such as network 120 and an API, and an API may enable interaction between the application program and device drivers and other aspects of the information handling system and software instructions 124 thereon. The computer system 100 may operate as a standalone device or may be connected, such as via a network 120, to other computer systems or peripheral devices.

Main memory 104 may contain computer-readable medium (not shown), such as RAM in an example embodiment. An example of main memory 104 includes random access memory (RAM) such as static RAM (SRAM), dynamic RAM (DRAM), non-volatile RAM (NV-RAM), or the like, read only memory (ROM), another type of memory, or a combination thereof. Static memory 106 may contain computer-readable medium (not shown), such as NOR or NAND flash memory in some example embodiments. The disk drive unit 114, and the high-value data integration system 126 may include a computer-readable medium 122 such as a magnetic disk, or a solid-state disk in an example embodiment. The computer-readable medium of the memory 104, storage devices 106 and 114, and the high-value data integration system 126 may store one or more sets of instructions 124, such as software code corresponding to the present disclosure.

The disk drive unit 114, static memory 106, and computer readable medium 122 of the high-value data integration system 126 also contain space for data storage. Connector code sets, EdgeX Foundry™ compose files, EdgeX Foundry™ microservices containers may also be stored in part in the disk drive unit 114, static memory 106, or computer readable medium 122 of the high-value data integration system 126 in an embodiment. In other embodiments, data profile code sets, and EdgeX Foundry™ parameter values may also be stored in part or in full in the disk drive unit 114, static memory 106, or computer readable medium 122 of the high-value data integration system 126. Further, the instructions 124 of the high-value data integration system 126 may embody one or more of the methods or logic as described herein.

In a particular embodiment, the instructions, parameters, and profiles 124, and high-value data integration system 126 may reside completely, or at least partially, within the main memory 104, the static memory 106, disk drive 114, and/or within the processor 102 during execution by the information handling system 100. Software applications may be stored in static memory 106, disk drive 114, and the high-value data integration system 126.

The high-value data integration system 126 may also contain computer readable medium 122. While the computer-readable medium 122 is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding, or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to store information received via carrier wave signals such as a signal communicated over a transmission medium. Furthermore, a computer readable medium can store information received from distributed network resources such as from a cloud-based environment. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

The information handling system 100 may also include the high-value data integration system 126. The high-value data integration system 126 may be operably connected to the bus 108. The high-value data integration system 126 is discussed in greater detail herein below.

In other embodiments, dedicated hardware implementations such as application specific integrated circuits, programmable logic arrays and other hardware devices can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

When referred to as a "system", a "device," a "module," or the like, the embodiments described herein can be configured as hardware. For example, a portion of an information handling system device may be hardware such as, for example, an integrated circuit (such as an Application Specific Integrated Circuit (ASIC), a Field Programmable Gate Array (FPGA), a structured ASIC, or a device embedded on a larger chip), a card (such as a Peripheral Component Interface (PCI) card, a PCI-express card, a Personal Computer Memory Card International Association (PCMCIA) card, or other such expansion card), or a system (such as a motherboard, a system-on-a-chip (SoC), or a standalone device). The system, device, or module can include software, including firmware embedded at a device, such as a Intel® Core class processor, ARM® brand processors, Qualcomm® Snapdragon processors, or other processors and chipset, or other such device, or software capable of operating a relevant environment of the information handling system. The system, device or module can also include a combination of the foregoing examples of hardware or software. In an example embodiment, the high-value data integration system 126 above and the several modules described in the present disclosure may be embodied as hardware, software, firmware or some combination of the same. Note that an information handling system can include an integrated circuit or a board-level product having portions thereof that can also be any combination of hardware and software. Devices, modules, resources, or programs that are in communication with one another need not be in continuous communication with each other, unless expressly specified otherwise. In addition, devices, modules, resources, or programs that are in communication with one another can communicate directly or indirectly through one or more intermediaries.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

Figure 2:
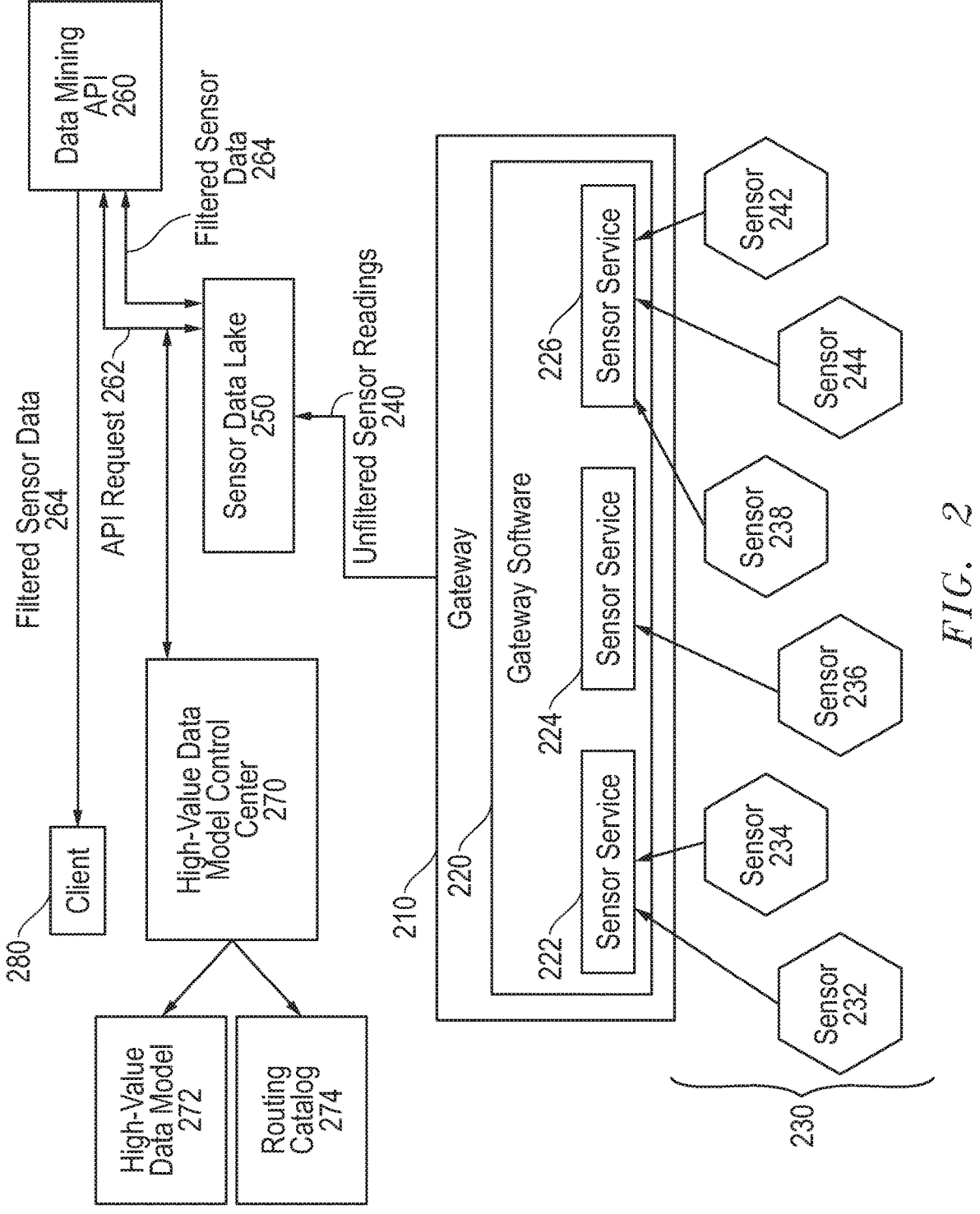
FIG. 2 is a block diagram illustrating a sensor data environment according to the present disclosure.

FIG. 2 is a block diagram illustrating a sensor data environment with a gateway operatively coupled to a plurality of sensors according to the present disclosure. Today, enterprises typically have a large IT infrastructure comprising a network of computing resources distributed across a geographic environment, including IoT networks. For example, a given IoT network may include sensors that monitor one or more conditions in one or more environments in which they reside by collecting data and providing data (either raw collected data and/or data processed by the sensor) to one or more computing nodes, i.e., gateways, associated with the enterprise or other entity. The term "gateway" is intended to be broadly construed so as to encompass, for example, a computing node that enables data communication between at least two discrete networks. In illustrative embodiments, a gateway enables data communication between a network of sensors and a cloud computing platform. However, embodiments are not limited to sensor/cloud scenarios.

A sensor data environment in an embodiment may include a gateway 210, operating gateway software 220 to communicate with a plurality of sensors 230. The gateway 210 in an embodiment may be a computing node that enables data communications between at least two discrete networks. In an embodiment, gateway 210 may enable data communication between a network of sensors 230 and one or more clients, or a cloud computing platform.

The gateway 210 in an embodiment may operate gateway software 220, which may at least partially include EdgeX Foundry™ (the Linux Foundation®) software which provides an open source microservices framework that allows a connection and execution environment for edge devices (e.g., sensors 230 operatively coupled to gateway 210). It is contemplated that embodiments are not limited to any particular gateway software product. Further, gateway 210 may be communicatively coupled to a plurality of sensors 230, including a variety of sensor types. For example, sensors 232, and 238 may comprise thermostats, sensor 234 may comprise a motor, sensor 236 may comprise a motion detector, sensor 244 may comprise a camera, and sensor 242 may comprise a light sensor (e.g., UV, infrared, or visible light).

There is a significant need to aggregate or integrate various types of continuously streaming sensor data at one or more locations within an enterprise network for analysis or notification of an event occurrence. Each of the plurality of sensors 230 in an embodiment may transmit data to one or more sensors services within the gateway software 220. For example, sensor service 222 may operate to import data from sensors 232 and 234, sensor service 224 may import data from sensor 236, and sensor service 226 may import data from sensors 238, 240, and 242. In other embodiments, sensors 230 may further include power meters, scales, robotics, actuation switches, capacity sensors, magnetic sensors, and electromagnetic sensors. The number of sensors and sensor services and their specific interconnectivity, as shown in FIG. 2, is for illustration purposes only. Alternative embodiments may have different numbers of sensors or sensor services connected in various alternative configurations.

In existing systems, management of the data processing and storage of sensor data is not optimized based on the value of such data to each subscribing client. Such mismanagement of resources may result in inefficiencies, including over publication of low-value sensor data. In such a scenario, the gateway 210 or gateway software 220 may publish to a subscribing client 280 sensor data (e.g., all sensor data received at one or more sensor services 222, 224, or 226), or sensor data filtered irrespective of the value of that sensor data to the subscribing client. This may inundate the subscribing client with large volumes of sensor data through which the client must sort to attain useful information.

In another example of mismanagement of resources, high-value sensor data may be under-distributed due to constrained or limited resources to perform processing, storage, and delivery of sensor data at the gateway. For example, clients who are unaware of the value of specific types of sensor data may fail to subscribe to receive such sensor data as the gateway software 220 receives it. As another example, sensor data may stream into the gateway 210 at a high frequency, causing automatic migration of older or more stale sensor data to a remote location. For example, sensor readings data 240 may be migrated to a remotely located sensor data lake 250, freeing memory space at the gateway 210. The sensor data lake 250 in existing systems may be located within the enterprise network, or within a cloud infrastructure.

Such a relocation of sensor data from the gateway 220 to the sensor data lake 250 may occur prior to or following publication of any of this sensor data 240 to a subscribing client. A subscribing client in existing systems may identify sensor data it would like to receive based on the type of sensor gathering the data (e.g., thermostat), identification of an individual device gathering the data (e.g., identified by MAC address), or on the field value of the data gathered (e.g., temperature, rather than humidity). The term "value" as used here in the context of client subscriptions and filtering of sensor data is not the same as the term "value" or "valuation" as in the context of a data valuation algorithm (value in the context of data evaluation algorithms may be financial or non-financial in nature as it relates to a given business, e.g., "business value"). Identification of which sensor data 240 to migrate to the sensor data lake 250 may be determined in existing systems based on the time of its recordation (e.g., migrating stale sensor data to free storage space for more recent sensor data), rather than any factors subscribing clients are likely to identify as determinative of the usefulness of such sensor data. Thus, the sensor data 240 migrated to the sensor data lake 250 may be unfiltered by client subscription topic.

Clients wishing to filter sensor data 240 stored at the sensor data lake 250 or to retrieve specific types of such sensor data 240 from the sensor data lake 250 may use a data mining application programming interface (API) 260. Such a data mining API 260 in existing systems may transmit requests for specifically identified types of sensor data readings stored at the sensor data lake 250. For example, a client 280 may communicate with data mining API 260 to describe the type of sensor data it wishes to receive using factors similar or identical to those traditionally found in client subscriptions (e.g., type of sensor gathering the data, identification of an individual device gathering the data, or field value of the data gathered). The data mining API 260 may then transmit a request 262 for sensor readings matching these descriptions, or described by such client-specified factors to the sensor data lake 250. The sensor data lake 250 may respond to this request 262 by transmitting one or more filtered sensor data readings 264 matching the client-specified description, and the data mining API 260 may forward the filtered sensor data readings 264 on to the client 280. Migrating sensor readings data 240 to the sensor data lake 250 and allowing clients 280 to mine the sensor data lake 250 using the API 260 in such a way may provide a potential solution to over-publication of sensor data, and storage restrictions at the gateway 210. However, this method does not differentiate between sensor data that is of high-value or low-value to the client 280.

In order to more efficiently manage such sensor data based on a valuation of the usefulness of the sensor data to a specific subscribing client 280, the high-value data integration system operating at a high-value data model control center 270 located within the enterprise network or hosted remotely in a cloud configuration in an embodiment may identify high-value data. The high-value data model control center 270 in an embodiment may also build a model to describe such data, and automatically develop application programming interfaces (APIs) that can automatically locate and distribute such high-value data or other sensor data similar to the identified high-value data at gateway 210 or at other gateways within the enterprise network.

In an embodiment, the high-value data integration system may identify high-value data by analyzing metadata associated with sensor readings that includes previously determined valuation scores for the sensor readings. For example, a data valuation framework of the high-value data integration system operating at the control center 270 may analyze the intercepted API requests 262 and existing client subscriptions to assign a valuation score to one or more sensor readings based on application of business logic and/or other data analytics, as described in greater detail with respect to FIG. 4A. Such a valuation framework may assign top-level business valuation scores to each sensor reading analyzed, and store such valuation scores in the metadata associated with the analyzed sensor readings and stored with the sensor readings persisted at the gateway 210.

The high-value data model control center 270 may then determine whether the filtered sensor data 264 is currently associated with a high-value data model describing the type of sensor gathering the data, identification of an individual device gathering the data, or field value of the data gathered. If a high-value data model is not currently associated with the filtered sensor data 264, the high-value data model control center 270 in an embodiment may then create a high-value data model 272 describing filtered sensor data 264. In another embodiment, the high-value data model control center 270 may also create high-value data model 272 to describe a sensor reading persisting at the gateway 210 associated with metadata that identifies the sensor reading as having a high valuation score, as assigned by a graphical-based data valuation framework. The structure and content of high-value data model 272 is described in greater detail herein with respect to FIG. 4A.

A data access catalog 274 may also be stored in an embodiment at the high-value model control center 270. In an embodiment, a data access catalog 274 may provide integrated technical metadata and business metadata associated with the filtered sensor data 264. For example, the integrated technical metadata and business metadata associated with the filtered sensor data 264 may provide information sufficient to trace the path filtered sensor data 264 takes through the several gateways, access points, or nodes of the enterprise network, as well as to identify each of a plurality of clients in receipt of the filtered sensor data 264 pursuant to subscription or API request 262. Such tracing information in an embodiment may assist in determining the value of the filtered sensor data 264 to each of a plurality of clients, or for a particular purpose, as described in greater detail with respect to FIG. 4B.

Figure 3:
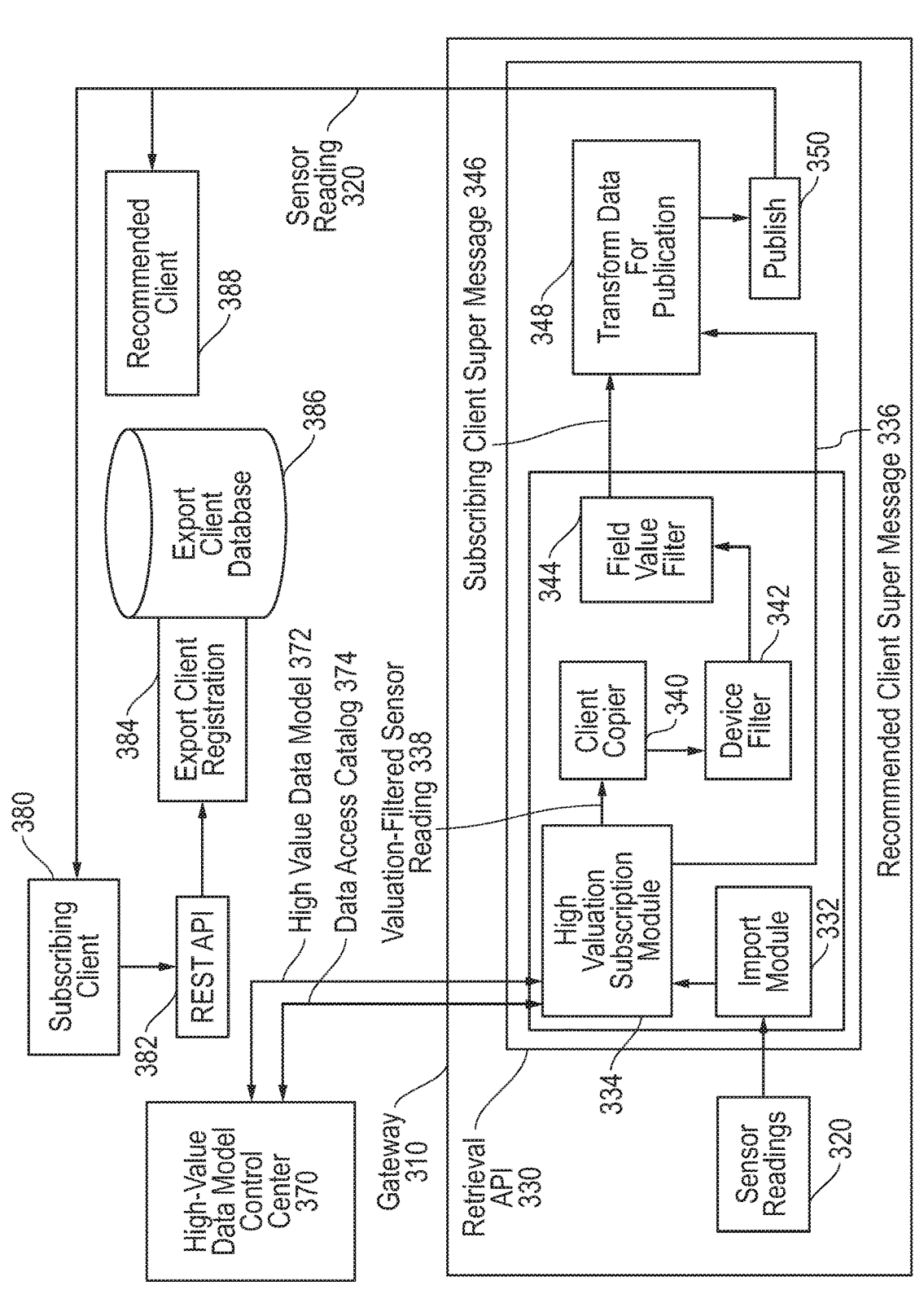
FIG. 3 is a block diagram illustrating communication between a gateway operating a high-value data integration system and a subscribing client in an embodiment according to the present disclosure.

FIG. 3 is a block diagram illustrating communication between a gateway operating a high-value data integration system and a subscribing client registered in an export client database in an embodiment according to the present disclosure. The high-value data model control center in embodiments may operate at least a portion of the high-value data integration system to automatically create a retrieval API capable of retrieving sensor data described by one or more fields of a stored high-value data model. Such a retrieval API may be installed at one or more gateways within an enterprise network, and may be used by any subscribing client to retrieve sensor data likely to be of high-value to that client. In such a way, the client may avoid having to download, customize, or maintain a separate data mining API, or to access and mine large pools of potentially stale sensor data stored in remote data lakes.

In an embodiment, the high-value data model control center 370 may create and transmit the retrieval API 330 for installation at gateway 310. In some embodiments, the retrieval API 330 may adhere to the vendor-agnostic open source EdgeX Foundry™ platform architecture developed by the Linux Foundation, that provides an open source microservices framework that allows a connection and execution environment for edge devices (e.g., IoT sensors in communication with gateway 310). It is to be appreciated that embodiments are not limited to any particular gateway service product. The EdgeX Foundry™ platform architecture may copy sensor data for transmission to each registered client, and filter the sensor data. As described herein, the high-value data integration system in embodiments herein may automatically generate a retrieval API by customizing a template EdgeX Foundry™ platform architecture to distribute only sensor readings identified as high-value based on descriptions given within a high-value data model.

The retrieval API 330 in an embodiment may include an import module 332 operating to access unfiltered sensor readings 320 persisting at the gateway 310. The import module 332 in an embodiment may receive a single sensor reading 320 in an embodiment, along with metadata associated therewith. The sensor reading 320 in an embodiment may correspond to one of the plurality of sensor readings data 240 described with respect to FIG. 2, as created, or recorded by the plurality of sensors 230 and persisted at gateway 210. In an embodiment, the retrieval API 330 may adhere to the EdgeX Foundry™ platform architecture, and the import module 332 may correspond to a microservices container (e.g., core data, metadata, or core command microservice container). The microservices container in such an embodiment may execute parameter values identifying the sensor reading 320, or a message queue operating at the gateway 310 where the IoT sensor device that recorded the sensor reading 320 places events or sensor readings as they occur or are recorded. These parameter values may not be unique to the retrieval API 330 in some embodiments, but rather, may follow known templates within the EdgeX Foundry™ platform architecture. The import module 332 may forward imported sensor reading 320 to a high-valuation subscription module 334 in an embodiment.

The high-valuation subscription module 334 in an embodiment may filter incoming or imported sensor readings based on valuation scores associated therewith. The high-valuation subscription module 334 in an embodiment at the gateway 310 may communicate with the high-value data model control center 370 to access a high-value data model 372 (e.g., corresponding to the high-value data model 272 described with respect to FIG. 2) or a data access catalog 374 associated with or describing the single sensor reading 320. The high-value data model 372 or the data access catalog 374 in an embodiment may be associated with or describe the single sensor reading 320 if a value stored in any one of the fields within the high-value data model 372 or data access catalog 374 matches a description of the single sensor reading 320.

In an embodiment, the retrieval API 330 may adhere to the EdgeX Foundry™ platform architecture, and the high-valuation subscription module 334 may correspond, at least in part, to a microservices container (e.g., a distribution microservice container). The distribution microservices container in an embodiment may execute customized parameter values to import the high-value data model 372 from a location within the high-value data model control center 370 or the gateway 310 at which the high-value data model 372 is stored. The high-value data model 372 in an embodiment may be transmitted from the high-value data model control center 370 for storage at the gateway 310. In other embodiments, the high-value data model 372 may be stored and accessed by the import module 322 at the high-value data model control center 370, which may be located remotely from the gateway 310 (e.g., at another location within the enterprise network, or within a cloud resource).

The high-valuation subscription module 334 in an embodiment may determine whether the sensor reading 320 is of high-value by identifying the valuation score in the high-value data model 372 associated with the sensor reading 320. If the valuation score meets a threshold value, the high-valuation subscription module in an embodiment may reference the data access catalog 374 to identify one or more clients who are not currently subscribed to receive the sensor reading 320, but who may benefit from receipt of the sensor reading 320, through a process described in greater detail with reference to FIGS. 4B and 6A. Such non-subscribing clients determined to potentially benefit from receipt of sensor reading 320 in such a way may be referred to herein as "recommended clients," as opposed to subscribing clients. Recommended clients identified in such a way in an embedment may only include clients authorized to receive sensor data 320. For example, only credentialed users having secure access to the enterprise network that includes gateway 310 may be considered as a potential recommended client in an embodiment.

The high-valuation subscription 334 in such an embodiment may prepare a "super message" for each recommended client. A super message in an embodiment may be an architectural design of the EdgeX Foundry™ platform architecture. In the existing EdgeX Foundry™ platform architecture, a super message may comprise an aggregation of the sensor reading 320, its metadata, and one or more export client registration records associated with subscribing clients, stored at the export client database 386. Super messages for recommended clients 336 in an embodiment may further include an identification of a recommended client, and the high-value data model 372 associated with the sensor reading 320. The high-valuation subscription module 334 may forward the recommended client super message 336 to the transformation module 348 to prepare the sensor reading 320 for delivery to the identified recommended client. 388. In such an aspect of an embodiment, the distribution microservices container corresponding to the high-valuation subscription module 334 may execute customized parameter values identifying the recommended client(s) to prepare such recommended client super message 336. In such a way, the high-valuation subscription module 334 in an embodiment may improve upon the functionality of the existing EdgeX Foundry™ platform architecture by identifying additional non-subscribing recipients that may benefit from receipt of the sensor reading 320, overcoming the inefficiency of under-publication of high-value data.

If the valuation score in the high-value data model 372 associated with the sensor reading 320 does not meet a high-value data threshold value, the high-valuation subscription module may determine whether the sensor reading 320 is of low-value. Clients may be subscribed to receive sensor reading 320, regardless of the valuation of such data, resulting in potential over-production of low-value data. In order to avoid this inefficiency, the high-valuation subscription module 334 in an embodiment may determine whether the valuation score in the high-value data model 372 falls below a preset low-value data threshold value, and filter out data readings having valuation scores below the threshold. In such an aspect of an embodiment, the distribution microservices container corresponding to the high-valuation subscription module 334 may execute customized parameter values comparing the valuation score against a preset low-value data threshold value. If the valuation score exceeds the low-value data threshold value in an embodiment, the sensor reading 320 may be forwarded on to the client copier 340. Such forwarded sensor reading 320 may be described herein as valuation-filtered sensor reading 338 in such a scenario, because the high-valuation subscription module 334 operates to filter out low-value data. The high-valuation subscription module 334 may discard the sensor reading 320 if the associated valuation score does not meet the low-value data threshold value, indicating the sensor reading 320 is of low-value. In such an embodiment, the sensor reading 320 may not be transformed, prepared for publication, or published to any subscribing or recommended clients. In such a way, the retrieval API 330 in an embodiment may avoid over-publication of low-value sensor readings.

A client copier module 340 in an embodiment may operate to identify one or more clients (e.g., 380) that have subscribed to receive sensor data persisting at gateway 310. A client may subscribe to receive sensor readings from a gateway in an embodiment by initiating a registration process. For example, client 380 in an embodiment may use a representational state transfer (REST) API 382 to communicate with an export client registration system 384 that persists client registration data on an export client database 386. The export client database 386 in an embodiment may store an association between the client 380 and the gateway 310. The client 380 may use the REST API 382 to add, update, and/or remove a client data registration in an embodiment. Client data registration in an embodiment may inform what, where, and how sensor readings should be distributed to registered software clients, including client 380 in an embodiment. Gateway 310 in some embodiments may operate according to a publish/subscribe model in which a client (e.g., client 380) subscribes to one or more topics describing various data readings. For example, client 380 may subscribe to a topic describing a type of IoT sensor, or a type of IoT reading. In another embodiment, gateway 310 may operate according to a push/pull model or a zero message queue (ZMQ) model.

The client copier 340 in an embodiment may receive the valuation-filtered sensor reading 338 from the high-valuation subscription module 334. The client copier 340 may then access a plurality of client subscription registration records stored at the export client database 386 in order to identify clients subscribing to receive the valuation-filtered sensor reading 338. In an embodiment, the retrieval API 330 may adhere to the EdgeX Foundry™ platform architecture, and the client copier module 340 may correspond to a microservices container (e.g., a client registration microservice container) of the uncustomized template EdgeX Foundry™ platform architecture. The client registration microservices container in such an embodiment may execute template parameter values drawn from existing architectures to identify the plurality of client registration subscription records, or locations within the export client database 386 at which the plurality of client registration subscription records are stored that describe sensor valuation-filtered sensor reading 338.

Each client registration subscription record in an embodiment may include one or more fields describing a type of sensor data reading the client would like to receive. For example, a client registration subscription record in an embodiment in which the retrieval API 330 adheres to the EdgeX Foundry™ platform architecture may identify sensor data gathered by a type of sensor (e.g., a thermostat), sensor data gathered by a specific sensor (e.g., identified by MAC address), or a specific type of sensor reading (e.g., temperature). Embodiments of the present disclosure may improve upon the EdgeX Foundry™ platform architecture by allowing subscribing clients to further describe sensor readings within their associated client registration subscription records by firmware operating at the sensor device gathering data, the gateway at which the sensor data is persisted, and whether the sensor data has any access restrictions. If the valuation-filtered sensor reading 338 can be described by any one of these fields in a given client's registration subscription record, the client copier 340 in an embodiment may identify that client as a subscribing client.

The client copier 340 may identify a plurality of subscribing clients, including client 380, in such a way. Subscribing clients identified in such a way in an embedment may only include clients authorized to receive sensor data 320. For example, only credentialed users having secure access to the enterprise network that includes gateway 310 may be considered as a potential subscribing client in an embodiment. The client copier 340 in an embodiment may create a separate "super message" for each of the subscribing clients. This super message may include the valuation-filtered sensor reading 338, and one client subscription registration record associated with one of the plurality of subscribing clients. The field values within each client subscription registration record may be used to filter data toward specific subscribing clients in an embodiment. The client copier 340 may forward such a super message on to the device filter module 342 in an embodiment.

The device filter module 342 in an embodiment may operate to filter out super messages that include sensor readings to which the subscribing client identified in the super message is not subscribed. As described herein, the client copier 340 in an embodiment may have identified a client as a subscribing client, and thus created a super message associated with that client, if the valuation-filtered sensor reading 338 can be described by any one of the fields in a given client's registration subscription record. The device filter module 342 in an embodiment may identify the device that recorded the valuation-filtered sensor reading 338 in the metadata included within such a super message, and discard the entire super message if that same device is not also identified in the client registration subscription record included within the super message. The device description in such an embodiment may identify the type of device, or the specific identity of an individual device. In such a way, the retrieval API 330 may narrow the number of super messages requiring further processing.

The field value filter module 344 in an embodiment may receive any super messages not discarded by the device filter module 342 in an embodiment. In an embodiment, the field value filter module 344 may operate to identify the type of reading in a super message, and discard the entire super message if that same reading type is not also identified in the client registration subscription record included within the super message. The reading field value within the valuation-filtered sensor reading 338 in such an embodiment may identify the type of reading. In such a way, the retrieval API 330 may further narrow the number of super messages requiring further processing.

The field value filter module 344 in an embodiment may transmit the remaining (e.g., non discarded) subscribing client super messages 346, each containing the valuation-filtered sensor reading 338 and at least one client registration subscription record to the transformation module 348. The transformation module 348 may also receive recommended client super messages 336 from the high-valuation subscription module 334. The subscribing client super messages 346 and recommended client super messages 336 may be transformed (e.g., compressed, encrypted, etc.) before being sent to each of the registered clients and recommended clients, respectively, via the publication module 350. In some embodiments, the transformation module 348 may perform encryption or other access restriction methods to ensure access to the sensor reading 320 included within a recommended client super message 336 is restricted in accordance with the access restrictions identified in the high-value data model 372 also included in the recommended client super message 336. The publication module 350 in an embodiment may identify the subscribing client for each received subscribing client super message 346, and may transmit the sensor reading 320, as transformed by the transformation module 348 to the identified subscribing client (e.g., 380). In another aspect of an embodiment, the publication module 350 may identify the recommended client for each received recommended client super message 336, and may transmit the sensor reading 320, as transformed by the transformation module 348 to the identified recommended client (e.g., 388). In such a way, the high-valuation subscription module may improve upon existing EdgeX Foundry™ platform architecture by avoiding over-distribution of low-value sensor readings to subscribing clients (e.g., 380), and by distributing high-value sensor readings to non-subscribing, but recommended clients (e.g., 388), thus remedying under-distribution of high-value sensor readings.

Figure 4A:
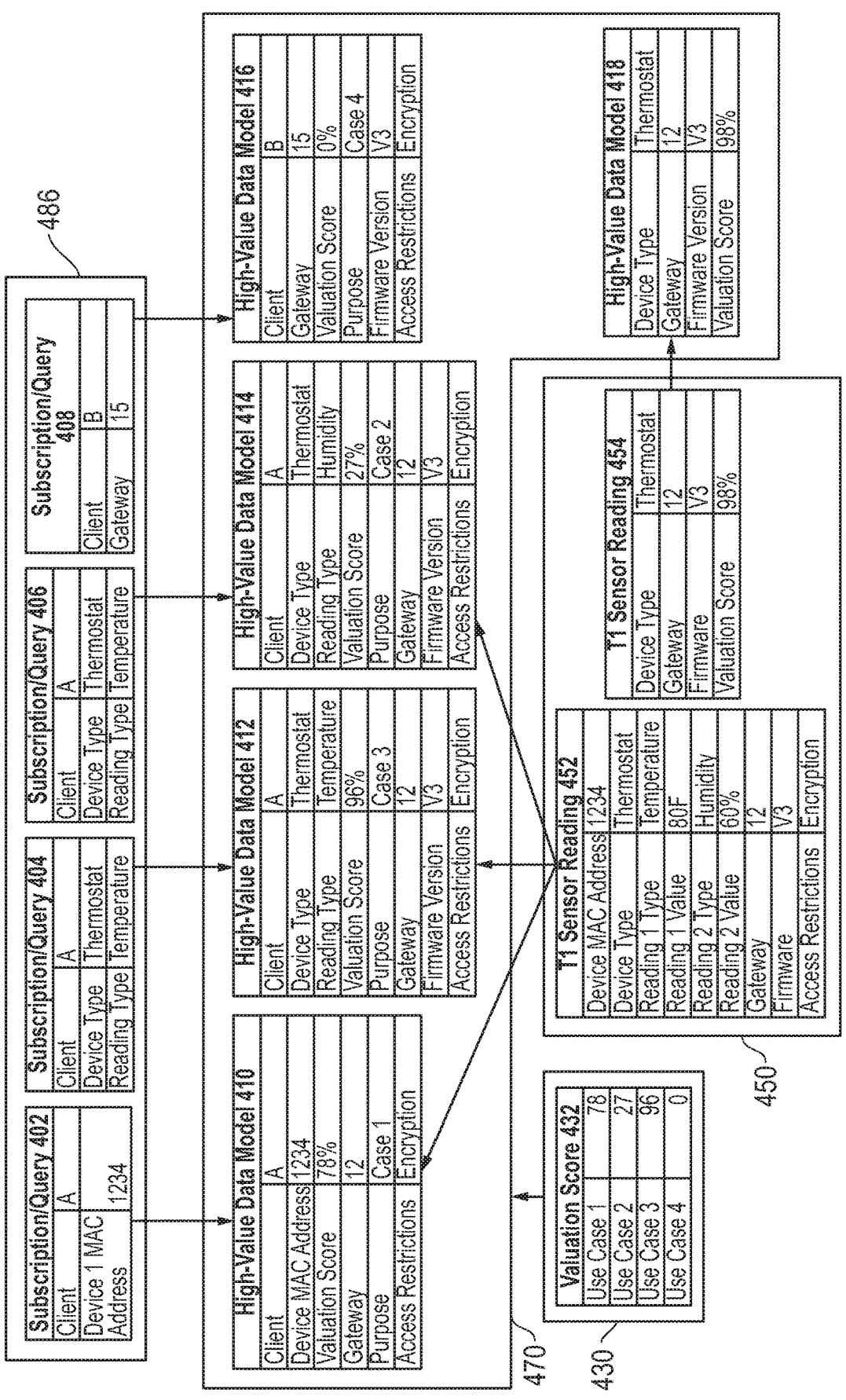
FIG. 4A is a block diagram illustrating formation of a high-value data model according to an embodiment of the present disclosure.

FIG. 4A is a block diagram illustrating data structures integrated together in formation of a high-value data model according to an embodiment of the present disclosure. As described herein, the high-value data integration system in an embodiment may identify high-value data, in order to more efficiently manage such sensor data based on a valuation of the usefulness of the sensor data to a specific subscribing client. The high-value data integration system in an embodiment may also build a model to describe such data.

In an embodiment, the high-value data integration system may identify high-value data by analyzing sensor reading transmitted pursuant to client subscription records, data mining API queries and requests intercepted between a client and a data lake, or metadata associated with sensor readings that includes previously determined valuation scores for the sensor readings. In some embodiments, the high-value data integration system in an embodiment may access a plurality of client registration subscription records persisted at an export client database 486 (corresponding to the export client database 386 described with reference to FIG. 3). In another embodiment, the high-value data integration system in an embodiment may intercept one or more API calls from a data mining API to identify data records of interest to existing clients.

The intercepted API calls and client registration subscription records in an embodiment may contain similar data, including an identification of the client subscribing to receive or requesting delivery of a sensor reading. In some embodiments, the intercepted API calls and client registration subscription records in an embodiment may also include one or more of an identification of the device that recorded the sensor reading (by type or by ID), the type of sensor reading, or the gateway at which the sensor reading first entered the enterprise network. For example, a subscription/query 402 in an embodiment may identify client A having received or being subscribed to receive a sensor reading from a sensor device having a MAC address "1234." MAC addresses actually include 48 bit values. To simplify representation of a MAC address in FIG. 4A, the symbolic or representative value "1234" is used in place of a 48 bit value in compliance with actual MAC address formatting. As another example, a subscription/query 404 in an embodiment may identify client A having received or being subscribed to receive a temperature sensor reading from a thermostat sensor device. As yet another example, a subscription/query 406 in an embodiment may identify client A having received or being subscribed to receive a humidity sensor reading from a thermostat sensor device. In still another example, a subscription/query 408 in an embodiment may identify client B having received or being subscribed to receive all sensor readings imported into a gateway identified as gateway 15.

The high-value data integration system in an embodiment may create a high-value data model to describe data previously requested by subscribing or data-mining clients. A separate high-value data model may be created for each subscription/query record stored at the export client database 486 or intercepted from a data-mining API in an embodiment. For example, the high-value data integration system may create a high-value data model 410 in an embodiment to describe the sensor readings requested by client A within the subscription query 402. More specifically, the high-value data model 410 may identify client A, and the device MAC address 1234 based on analysis of the subscription/query 402. As another example, the high-value data integration system may create a high-value data model 412 in an embodiment to identify client A, the device type thermostat, and the reading type temperature, based on analysis of the subscription/query 404. As yet another example, the high-value data integration system may create a high-value data model 414 in an embodiment to identify client A, the device type thermostat, and the reading type humidity, based on analysis of the subscription/query 406. In still another example, the high-value data integration system may create a high-value data model 416 in an embodiment to identify client B, and gateway 15, based on analysis of the subscription/query 408.

In other embodiments, a single high-value data model may incorporate descriptions of data from a plurality of subscriptions/queries. A single high-value data model in such an embodiment may describe an individual sensor reading, which may be responsive to a plurality of subscriptions/queries. For example, a single high-value data model in such an embodiment may describe a temperature reading and a humidity reading, both received from the same thermostat sensor. In such an example, the temperature reading may be responsive to a first subscription/query, and the humidity may be responsive to a second, separate subscription/query.

The high-value data models in an embodiment may be stored at a high-value data model control center 470 (corresponding to the control center 370 described with reference to FIG. 3), and may be transmitted to one or more gateways of the enterprise network upon request. For example, the control center 470 in an embodiment may transmit high-value data models to a retrieval API operating at a gateway 450 within the enterprise network. As described herein, the high-value data integration system in an embodiment may automatically generate and deliver a retrieval API for installation at gateway 450 of the enterprise network.

Such a retrieval API in an embodiment may request and receive one or more high value data models (e.g., 410, 412, 414, or 416), based on similarities between such high value data models and sensor readings received at the gateway 450 operating the retrieval API. For example, a gateway 450 operating a retrieval API may receive a sensor reading 452 recorded at a first time "T1." The retrieval API in such an embodiment may then determine whether the T1 sensor reading 452 is associated with any already existing high-value data models. The T1 sensor reading 452 may be associated with an already existing high-value data model in an embodiment if one or more descriptors within the T1 sensor reading 452 match any one or more of the descriptors within a high-value data model. For example, the retrieval API may determine both the T1 sensor reading 452 and the high-value data model 410 contain the descriptor "1234" as the device MAC address. As another example, the retrieval API may determine both the T1 sensor reading 452 and the high-value data model 412 describe temperature readings from a thermostat sensor. As yet another example, the retrieval API may determine both the T1 sensor reading 452 and the high-value data model 414 describe humidity readings from a thermostat sensor.

In other embodiments, the retrieval API may determine the received sensor reading is not associated with or described by any existing high-value data models. In such a scenario, the retrieval API operating at the gateway 450 may transmit the sensor reading and associated metadata (e.g., including valuation score information) to the control center 470 for creation of a new high-value data model. For example, in an embodiment in which the retrieval API operating at the gateway 450 determines sensor reading 454 received at time "T1" is not described by or associated with any high-value data models stored at the 470 or at the gateway 450, the retrieval API operating at the gateway 450 may transmit the sensor reading 454 to the control center 470, where the high-value data model 418 may be generated. More specifically, the high-value data model 418 may identify sensor readings taken from a thermostat sensor in communication with gateway 12, which may be operating version 3 of the firmware.

In another aspect of an embodiment, the retrieval API operating at gateway 450 may also determine whether metadata associated with received sensor readings includes information not yet described in the high-value data model associated with the received sensor. As described herein, the metadata associated with a received sensor reading in an embodiment may also include valuation scores evaluating the usefulness of the sensor reading for preset and known purposes or uses. Data valuations in an embodiment may be performed on individual sensor readings by a graphical-based data valuation framework to assign a business-level valuation to the sensor reading based on workflow and usage of the content within such a sensor reading. For example, one or more data valuation systems persisted at the control center 470 in an embodiment may track business logic and data analytic activity associated with the sensor reading 452, assign one or more top-level business valuation scores 432 to one or more uses for the sensor reading 452, and cascade that valuation score 432 back down to the gateway 450 that initially imported the sensor reading 452. The valuation scores 432 in such an embodiment may be stored within the metadata of the sensor reading 452 at gateway 450, or may be stored in a separate record 430 associated with sensor reading 452.

The data valuation systems (not shown) persisted at the control center 470 in an embodiment may assign the valuation score to an individual sensor reading in such a way using any known method of data asset valuation, including financial and non-financial models, metadata-based data valuation, asset usage based methods, and business-relevance based models. Financial methods may include, for example, a cost value of information model, representing a measure of the cost of losing the data, or a market value of information model, representing a measure of a value of the amount that could be obtained by selling or trading the data set. In another example, financial methods may include an economic value of information model, representing a measure of a value of how the data set contributes to a financial bottom line. Non-financial methods may include, for example, an intrinsic value of information model, representing a measure of a value of the correctness, completeness, and exclusivity of the data set, or a performance value of information model, representing a measure of a value of how the data set affects key business drivers.

In another example, non-financial methods may also include a business value of information model, representing a measure of a value of the sufficiency and relevance of the data set for specific purposes. As shown in the valuation score 432, for example, a business value of information model may assign a valuation score to one or more specific purposes or use cases for application of a sensor reading 452. Use cases in an embodiment may describe any specific purpose or usage of the sensor reading by any end client within the enterprise network. A business value of information model in an example embodiment may be used to assign a valuation score to sensor reading 452, specifically describing the usefulness of reading 452 for the purpose of improving accuracy of a determination made based on a plurality of sensor readings, including sensor reading 452. For example, sensor reading 452 may include a temperature measurement made by one of a plurality of thermostat sensors within the enterprise network. Temperature measurements made by each thermostat sensor in the network may have a margin of error. The accuracy of a determination of an average temperature made based on a plurality of such temperature measurements may increase as the number of thermostat sensors recording such measurements increases.

A valuation score in an embodiment may also be assigned to sensor reading 452 specifically describing the usefulness for the purpose of limiting transmission of sensor readings between a first IoT sensor and a second IoT sensor within the enterprise network to only include sensor readings upon which the second IoT sensor may act. For example, the first IoT sensor in such an embodiment may be a thermostat sensor capable of recording temperature and humidity measurements, and the second IoT sensor may be an IoT motor set to operate within a specific range of temperatures. In such an example embodiment, it may increase efficiency of the first and second IoT sensors to limit the volume of data readings transmitted from the first thermostat IoT sensor to the second motor IoT sensor to only include the temperature readings, since the second IoT sensor only needs the temperature readings to determine whether the motor should be turned on or off.

A business value of information model in yet another example embodiment may be used to assign a valuation score to sensor reading 452, specifically describing the usefulness of reading 452 for the purpose of identifying, performing maintenance upon, or repairing a defective IoT sensor. In an example embodiment, the thermostat sensor that recorded sensor reading 452 in an embodiment may be only one of several other thermostat sensors situated nearby one another. The temperature reading of 80 degrees Fahrenheit in sensor reading 452 in such an example embodiment may indicate the thermostat sensor that recorded reading 452 is malfunctioning if all of the other nearby IoT thermostat sensors are consistently reading a much lower or much higher temperature. In another example embodiment, if a malfunction is suspected, or a routine maintenance update is required among one of a plurality of IoT sensors operating within the enterprise network, analysis of the firmware versions that are running on each of these IoT sensors (as shown in sensor reading 452) may reveal an IoT sensor malfunctioning, or needed maintenance due to firmware operating older versions of firmware than the other IoT sensors.

A valuation score in still another example embodiment may also be assigned to sensor reading 452 specifically describing the usefulness for a specifically identified software application or program. For example, a digital image processing application in an embodiment may perform digital processing on sensor readings that include images captured by camera sensors within an enterprise network. However, such a digital image processing application may not be capable of processing non-image sensor readings, such as temperature and humidity measurements. In such a scenario, the valuation score 432 associated with sensor reading 452 for the fourth use case, describing usefulness to a digital image processing application may be zero, or another relatively low number or value.

In some embodiments, the valuation score may take the form of a percentage value (e.g., from 0% to 100%). For example, in an embodiment, the valuation score 432 assigned to sensor reading 452 may indicate the sensor reading 452 is useful 78% of the time to improve accuracy of a determination made based on a plurality of sensor readings (e.g., use case 1). As another example, the valuation score 432 assigned to sensor reading 452 in an embodiment may indicate the sensor reading 452 is useful (e.g., in use case 2) to limit transmission of sensor readings between a first IoT sensor and a second IoT sensor within the enterprise network to only include sensor readings upon which the second IoT sensor may act 27% of the time. In yet another example, in an embodiment, the valuation score 432 assigned to sensor reading 452 may indicate the sensor reading 452 is useful 96% of the time to identify a defective IoT sensor (e.g., use case 3). In other embodiments, the valuation score may have other units, such as U.S. dollars or other currency value, time units such as seconds or minutes, or may be unitless.

The business value of information model in an embodiment may assign such valuation scores, in part, based on a determination of the relevance of a given sensor reading to each of the use cases, individual clients, or other business uses or purposes. One way of determining relevance of a given piece of information may include use of taxonomy mappings that associate business uses or specific clients with a list of keywords likely to be incorporated within information consumed for that business use of by that client. For example, an Extensible Markup Language (XML) file listing the words "shipping," "air," "flight," "sea," "tanker," "land," and "truck," may be associated with an inbound receivables logistics business unit. As another example, an Extensible Markup Language (XML) file listing the words "firmware," "alert," "flag," "failure," or "offline" may be associated with the third use case describing detection of malfunctioning IoT sensors.

In such an embodiment, once an identification of one or more such key terms within a sensor reading is made, the sensor reading may be associated with the business group, individual client, use case, or other categorization defined by those key words. The associated sensor reading and business group, individual client, use case, or other categorization in such an embodiment may then receive a valuation score describing the usefulness of that specific sensor reading to the specific business group, use case, or other categorization. In some embodiments, the valuation score associated with a given sensor reading may be determined based on the number of these terms identified within the sensor reading, or on the number of times previous sensor readings recorded by the sensor that also recorded the current sensor reading also included one or more of these terms.

In other embodiments, the business value of information model, or other models in an embodiment may assign such valuation scores to sensor readings (and associated business groups, individual clients, use cases, or other categorizations), in part, based on consumption of similar sensor readings through multiple levels of a hierarchical architecture of a value-based governance system. Such a hierarchical architecture may be an abstracted model of the flow, processing, and consumption of information between the sensor and the end client. The hierarchical architecture in an embodiment may include several layers, including an ingestion level, an innovation level, and a consumable level. For example, sensor readings to which clients have specifically subscribed, or that are specifically retrieved by a data mining API may be categorized in the "consumed" layer, because this evidences actual use of the sensor reading by an end client. As another example, sensor readings that have been imported into a gateway and processed for delivery to one or more clients may be categorized within the innovation level, regardless of whether the sensor reading actually reached an end client. In still another example, sensor readings that are imported into gateways, or pushed into data lakes, without undergoing pre-publication processing or transformation may fall into the "ingestion" layer. Placement of a sensor reading within one of these layers of the hierarchical architecture in an embodiment may determine the valuation score associated with the sensor reading, with the consumption layer indicating a higher valuation, and the ingestion layer indicating a lower valuation.

The valuation score assigned to an individual sensor reading in an embodiment may be made using any one of or any combination of these or any other known methods of information valuation. For example, the valuation score 432 in an embodiment may associate one or more portions of information within the sensor reading 452 with a valuation score of 78% with respect to use case 1, 27% with respect to use case 2, 96% with respect to use case 3, and 0% with respect to use case 4. Further, in some embodiments, each of these valuation scores may vary from client to client.

The valuation score 432 in an embodiment may be incorporated within one or more high-value data models at the control center 470. The valuation score 432 in an embodiment may be communicated to the control center 470 in an embodiment for incorporation within a new or pre-existing high-value data model. For example, the existing high-value data model 410 may identify the MAC address 1234, gateway number 12, and an encryption based access restriction method based on one or more fields of sensor reading 452. High-value data model 410 in such an embodiment may further identify Client A. It may be known, based on consumption of similar sensor readings by Client A through multiple levels of a hierarchical architecture of the value-based governance system, that Client A tends to consume sensor readings generated by the sensor with the MAC address 1234 specifically for the business use case 1. An association between Client A, sensor readings from the sensor with the MAC address 1234, and use case 1 may also be made, in other embodiments, based on analysis of a data access catalog, as described with reference to FIG. 4B.

Upon receipt of valuation score 432 at the control center 470 in an embodiment, the high-value data model 410 may be updated to include the valuation score of 78% for the business use case 1, indicating a 78% chance that sensor readings from MAC address 1234 will be useful to client A in improving accuracy of a determination made based on a plurality of sensor readings. In another example, the high-value data model 412 may be updated to include the valuation score of 96% for the business use case 3, indicating a 96% chance a temperature reading from a thermostat sensor may be useful to client A in identifying or repairing a defective IoT sensor. In yet another example, the high-value data model 414 may be updated to include the valuation score of 27% for the business use case 2, indicating a 27% chance a humidity reading from a thermostat sensor may be useful to client A in limiting transmission of sensor readings between a first IoT sensor and a second IoT sensor within the enterprise network to only include sensor readings upon which the second IoT sensor may act. In still another example, the high-value data model 416 may be updated to include the valuation score of 0% for the business use case 4, indicating very little or no chance that a sensor reading from an IoT sensor in communication with gateway 15 will be useful to Client B for a specifically identified software application or program. In such a way, the high-value data models in an embodiment may identify or gauge the usefulness of a sensor reading 452 received at a gateway 450 for a given purpose to a specific client.

Figure 4B:
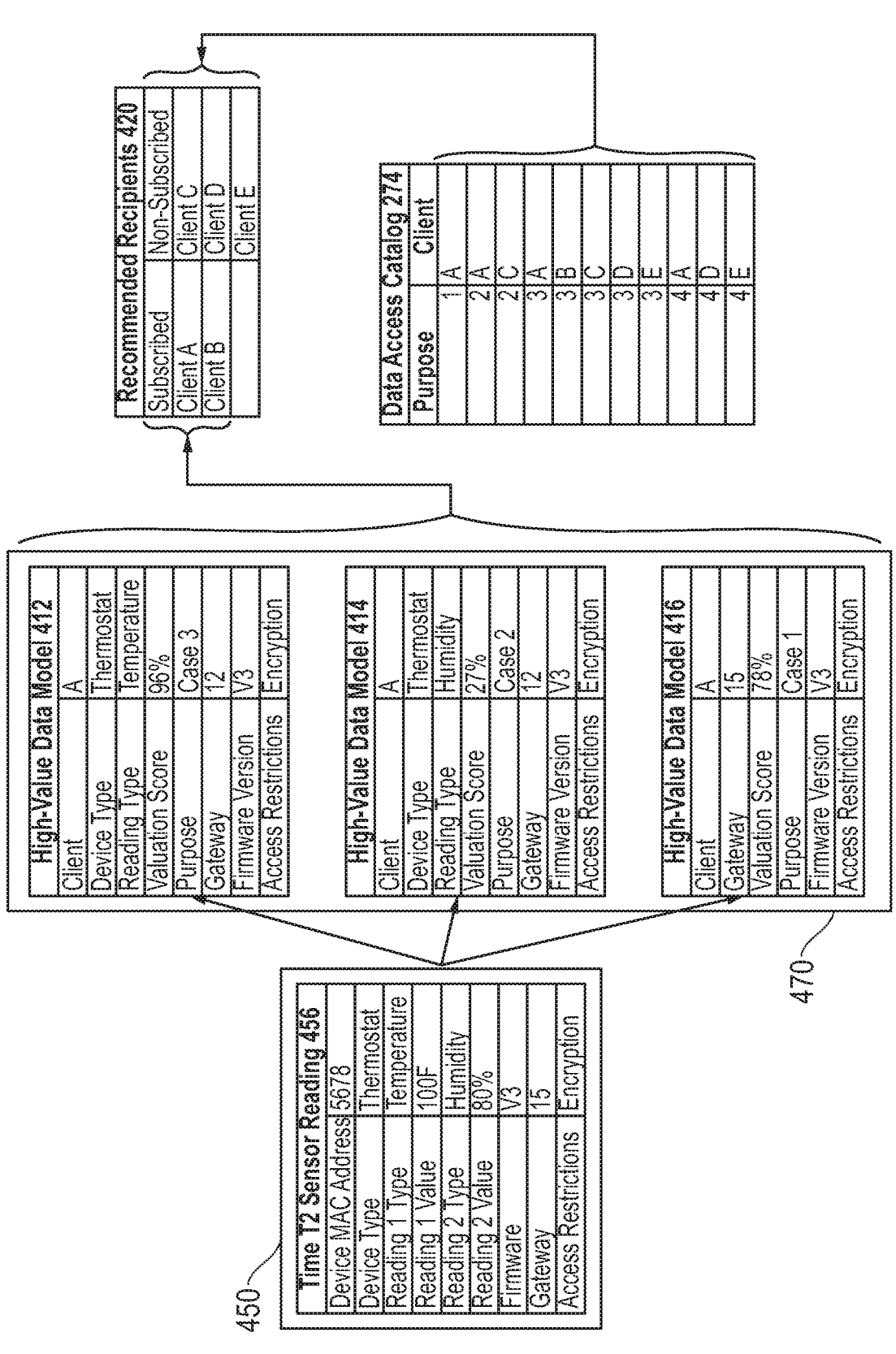
FIG. 4B is a block diagram illustrating formation of a list of recommended recipients according to an embodiment of the present disclosure.

FIG. 4B is a block diagram illustrating a high-value data model and data access catalog used in formation of a list of recommended recipients according to an embodiment of the present disclosure. Gateway 450 in an embodiment may receive a sensor reading 456 at a time T2, which may occur later in time than T1, at which the sensor reading 452 was recorded, as described with respect to FIG. 4A. In other words, sensor reading 452 may precede sensor reading 456 temporally. For example, sensor reading 456 may indicate a thermostat sensor with a MAC address of "5678", in communication with gateway 15 and running version 3 of firmware recorded a temperature of 100 degrees Fahrenheit and a humidity of 80% at time T2. Again, MAC addresses actually include 48 bit values. To simplify representation of a MAC address in FIG. 4B, the symbolic or representative value "5678" is used in place of a 48 bit value in compliance with actual MAC address formatting.

Upon receipt of the new sensor reading 456 in such an embodiment, the high-value data integration system operating at the gateway 450 may access one or more high-value data models stored at the control center 470 in order to identify one or more purposes, or business use cases for which new sensor reading 456 may prove useful. The high-value data integration system operating at the gateway 450 in an embodiment may identify one or more high-value data models at the control center 470 that describe, partially or in whole, the information within sensor reading 456. For example, the gateway 450 may determine the high-value data model 412 at control center 470 describes the T2 sensor reading 456 in that it identifies usefulness of temperature readings taken from a thermostat sensor running version 3 of the firmware. In another example, gateway 450 may determine the high-value data model 414 at control center 470 describes the T2 sensor reading 456 in that it identifies usefulness of humidity readings taken from a thermostat sensor running version 3 of the firmware. In still another example, gateway 450 may determine the high-value data model 416 at control center 470 describes the T2 sensor reading 456 in that it identifies usefulness of sensor readings imported into gateway 15.

Each of the high-value data models identified as describing the T2 sensor reading 456 in such a way may further identify a valuation score associated with that sensor reading 456 for a specific business purpose or use case. For example, high-value data model 412 may indicate the T2 sensor reading 456 is 96% likely to be useful in use case 3, for the purpose of identifying or repairing a defective IoT sensor. As another example, high-value data model 414 may indicate the T2 sensor reading 456 is 27% likely to be useful in use case 2, for the purpose of limiting transmission of sensor readings between a first IoT sensor and a second IoT sensor within the enterprise network to only include sensor readings upon which the second IoT sensor may act. As yet another example, high-value data model 412 may indicate the T2 sensor reading 456 is 78% likely to be useful in use case 1, for the purpose of improving accuracy of a determination made based on a plurality of sensor readings.

The high-value data integration system operating at gateway 450 in an embodiment may then access a data access catalog 274 to identify clients that are not subscribed to receive sensor reading 456, but who are also likely to benefit from using sensor reading 456 in use cases 1, 2, or 3. As described herein, in an embodiment, a data access catalog 274 may provide integrated technical metadata and business metadata associated with sensor reading 452, upon which the high-value data models 412, 414, and 416 were built. For example, the integrated technical metadata and business metadata associated with the filtered sensor data 264 may provide information sufficient to trace the path sensor reading 452 takes through the several gateways, access points, or nodes of the enterprise network, as well as to identify each of a plurality of clients in receipt of the filtered sensor data 264 pursuant to subscription or API request 262. The data access catalog 274 in an embodiment may associate a plurality of business units, working groups, use cases, or other logical categorizations with one or more individual clients. For example, the data access catalog 374 may associate business use case 1 with client A, business use case 2 with clients A and C, business use case 3 with clients A, B, C, D, and E, and business use case 4 with clients A, D, and E. In other embodiments, the data access catalog 274 may associate an individual business use case with one or more business units or working groups.

The high-value data integration system operating at the gateway 450 in an embodiment may identify that clients A and B are already subscribed to receive T2 sensor reading 456, based on access to client subscription registration records (as described with reference to FIGS. 3 and 4A), or by reference to the high-value data models 412, 414, and 416 specifically identifying client A as a subscriber to similar sensor readings. The high-value data integration system in such an embodiment may also reference the data access catalog 274 to identify one or more recommended (but non-subscribing clients) that would also benefit from receipt of at least a portion of T2 sensor reading 456. For example, the high-value data integration system in an embodiment may identify one or more business use cases for which high-value data model describing the T2 sensor reading 456 received a valuation score meeting or exceeding a high-value threshold. The high-value threshold in an embodiment may be a preset value, and may depend upon the units used to define the valuation score. For example, in an embodiment in which valuation scores are given as a percentage from zero to 100, the high-value threshold may be 90%. In such an example embodiment, the high-value data integration system may determine the valuation scores of 27% and 78% associated with high-value data models 414 and 416, respectively, do not meet the high-value threshold. However, the high-value data integration system in such an example embodiment may determine the valuation score of 96% associated with high-value data model 412 does meet the high-value threshold.

Upon identification of a high-value data model having a valuation score that meets or exceeds the high-value threshold in an embodiment, the high-value data integration system operating at the gateway 450 may determine whether any non-subscribing clients are associated within the data access catalog 274 with the use case identified in the high-value data model. For example, the high-value data integration system may identify the valuation score 96% within the high-value data model 412 in an embodiment is associated with the use case 3. The high-value data integration system in such an embodiment may also determine, by referencing the data access catalog 274 that non-subscribing clients C, D, and E are associated with business use case 3. This may indicate a high likelihood that clients C, D, and E may benefit from use of T2 sensor reading 456 in identifying or repairing a defective IoT sensor. The high-value data integration system in an embodiment may list the non-subscribing clients C, D, and E identified in such a manner as recommended recipients in a data record 420. In such a way, the high-value data integration system may identify clients not subscribed to receive a sensor reading as a recommended recipient, based on likelihood such sensor reading may be useful to that recipient, thus avoiding under-publication of high-value sensor readings.

Figure 5:
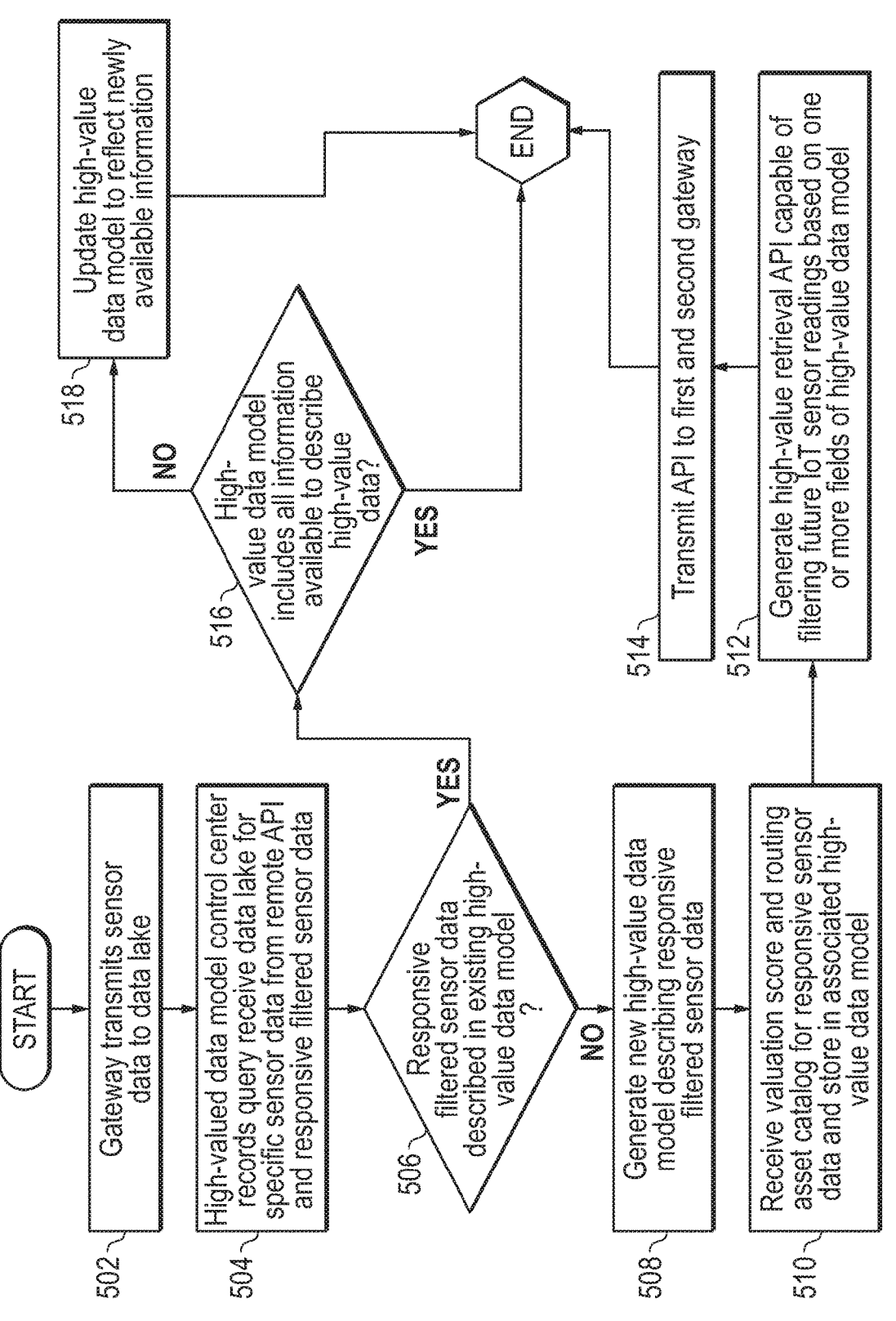
FIG. 5 is a flow diagram illustrating a method of automatically creating a retrieval Application Programming Interface (API) for retrieving high-value sensor data according to the present disclosure.

FIG. 5 is a flow diagram illustrating a method of automatically creating a high-value data model and creating a retrieval Application programming interface (API) for retrieving high-value sensor data according to the present disclosure. In order to efficiently manage a high volume of incoming IoT sensor data, it may be beneficial to devote more resources to the processing and storage of higher value sensor data, rather than sensor data that is rarely used or leveraged by subscribing clients. In existing systems, management of IoT sensor data processing and storage is not optimized based on such valuations. The high-value data integration system in embodiments of the present disclosure may address these issues by identifying high-value data, building a model to describe such data, and automatically developing application programming interfaces (APIs) that can automatically locate and distribute such high-value data or other sensor data similar to the identified high-value data.

At block 502, a gateway device where IoT sensor data is gathered and persisted may transmit sensor data to a data lake for long term storage. For example, in an embodiment described with reference to FIG. 2, gateway 210 may enable data communication between a network of sensors 230 and one or more clients, or a cloud computing platform. Sensor data may stream into the gateway 210 at a high rate or volume, causing automatic migration of older or more stale sensor data to a remotely located sensor data lake 250, freeing memory space at the gateway 210. Migrating sensor readings data 240 to the sensor data lake 250 and allowing clients 280 to mine the sensor data lake 250 using the API 260 in such a way may provide a potential solution to over-publication of sensor data, and storage restrictions at the gateway 210.

The high-value data integration system operating at least in part at a high-value data model control center in an embodiment may intercept a request from a remote or third-party API for specifically described sensor data persisted at the data lake at block 504. For example, in an embodiment described with respect to FIG. 2, API 260 in existing systems may transmit requests for specifically identified types of sensor data readings stored at the sensor data lake 250. Client 280 may communicate with data mining API 260 to describe the type of sensor data it wishes to receive using factors similar or identical to those traditionally found in client subscriptions (e.g., type of sensor gathering the data, identification of an individual device gathering the data, or field value of the data gathered). The data mining API 260 may transmit a request 262 for sensor readings matching these descriptions, or described by such client-specified factors to the sensor data lake 250.

The high-value data integration system operating at least in part at a high-value data model control center in an embodiment may also intercept one or more sensor readings responsive to this request, as transmitted from the sensor data lake 250 to the API 260 in an embodiment. The sensor data lake 250 may respond to this request 262 by transmitting one or more filtered sensor data readings 264 matching the client-specified description, and the data mining API 260 may forward the filtered sensor data readings 264 on to the client 280.

In other embodiments, the high-value data integration system may intercept one or more sensor readings transmitted to an end client pursuant to a subscription. For example, in an embodiment described with reference to FIG. 4A, the high-value data integration system operating at a control center 470 may access a plurality of client registration subscription records persisted at an export client database 486 or may intercept one or more API calls from a data mining API to identify subscription/query 402, 404, 406, or 408. In another aspect, the high-value data integration system operating at the gateway 450 in an embodiment may receive T1 sensor reading 452 at block 504, which may be responsive to one or more subscriptions/queries 402, 404, 406, or 408. Receipt of T1 sensor reading 452 in such an embodiment may be functionally equivalent to interception of a sensor reading transmitted from the data lake to the data mining API pursuant to an API call.

In still other embodiments, the high-value data integration system operating at the gateway 450 in an embodiment may receive T1 sensor reading 454 at block 504. Sensor readings 452 and 454 in such an embodiment may have been recorded simultaneously, from two separate thermostat sensors in communication with gateway 12, for example. T1 sensor reading 454 in such an embodiment may be associated with a valuation score of 98%, indicating that T1 sensor reading 454 is of high-value for one or more use cases or business purposes.

At block 506, the high-value data integration system operating at least in part at the high-value data model control center in an embodiment may determine whether the responsive sensor data transmitted back to the API is described in a currently existing high-value data model. Identifying sensor data that is likely to be of high-value to a subscribing client may allow enterprises to more effectively leverage that value in an embodiment. The high-value data integration system in an embodiment may identify such high-value data and create a data model describing such high-value data, such that later retrieval of future similar readings may be completed automatically or more easily.

Presumably, client 280 would mine the sensor data lake 250 in order to locate only data readings having a relatively higher valuation or usefulness to client 280. As such, any filtered sensor data 264 mined by the API 260 pursuant to the request 262 may be identified in an embodiment as having a high valuation score. In other embodiments, sensor readings received at the gateway may be associated with valuation scores indicating the sensor reading is of high value for at least one use case or business purpose. If such high-value sensor data is not already associated with a high-value data model, the method may proceed to block 508 for creation of such a high-value data model. If the high-value sensor data is already associated with a high-value data model, the method may proceed to block 516 to determine whether any description of received sensor data should be added to the existing high-value data model.

Returning to FIG. 5, at block 508, the high-value data integration system operating at least partially at the high-value data model control center in an embodiment in which no high-value data model exists to describe the high-value sensor data may create a new high-value data model describing the high-value sensor data. For example, in an embodiment described with reference to FIG. 2, the high-value data model 272 may include all information described in the sensor reading and its associated metadata, and may identify the gateway 210 at which the sensor reading was collected, the firmware operating at the sensor that collected the sensor reading, and whether access restrictions apply to the sensor data.

As another example, in an embodiment described with respect to FIG. 4A, the high-value data integration system operating at either the gateway 450 or the control center 270 may determine the T1 sensor reading 454 received at the gateway 450 at block 504 is not currently associated with a high-value data model. In such an embodiment, the high-value data integration system operating at the gateway 450 may transmit the T1 sensor reading 454, along with its metadata to the control center 470. The high-value data integration system operating at the control center 470 in such an embodiment may create high-value data model 418, describing the T1 sensor reading 454. In other embodiments, the high-value data integration system operating at the gateway 450 may create the high-value data model 418 describing T1 sensor reading 454, and transmit the high-value data model 418 to the control center 470 for storage.

As another example, in an embodiment described with reference to FIG. 4A, the high-value data integration system operating at control center 470 may determine a high-value data model does not exist to describe one or more of subscription/queries 402, 404, 406, or 408. The high-value data integration system in such an embodiment may thus create high-value data model 410 to describe subscription/query 402, high-value data model 412 to describe subscription/query 404, high-value data model 414 to describe subscription/query 406, or high-value data model 416 to describe subscription/query 408.

At block 510, in an embodiment, the high-value data integration system operating at least in part on the high-value data model control center may receive a valuation of the high-value sensor data. In some such embodiments, data valuations in an embodiment may be performed on individual sensor readings by a graphical-based data valuation framework to assign a business-level valuation to the sensor reading based on workflow and usage of the content within such a sensor reading. For example, one or more data valuation systems persisted at the control center 470 in an embodiment may track business logic and data analytic activity associated with the sensor reading 452, assign one or more top-level business valuation scores 432 to one or more uses for the sensor reading 452, and cascade that valuation score 432 back down to the gateway 450 that initially imported the sensor reading 452. The valuation scores 432 in such an embodiment may be stored within the metadata of the sensor reading 452 at gateway 450, or may be stored in a separate record 430 associated with sensor reading 452.

Returning to FIG. 5, the high-value data integration system operating at least partially at the high-value data model control center in an embodiment may create a high-value retrieval API capable of filtering future IoT sensor readings based on one or more fields of the high-value data model at block 512. For example, in some embodiments, the gateway 210 may operate gateway software 220, which may at least partially include EdgeX Foundry™ software providing an open source microservices framework that allows a connection and execution environment for edge devices (e.g., sensors 230 operatively coupled to gateway 210). The retrieval API automatically created by the high-value data integration system may also adhere to the EdgeX Foundry™ platform architecture, and may automate the process of identifying high-value sensor data, filtering such data, and processing it for delivery to subscribing clients that may find the data useful or of high-value. Description of the functionality of such a retrieval API is described in further detail herein with respect to FIGS. 3, 6A, and 6B.

At block 514, the high-value data integration system operating at least partially at the high-value data model control center in an embodiment may transmit the retrieval API created at block 512 to one or more gateways within the enterprise network. For example, in one embodiment described with reference to FIG. 2, the high-value data model 272 may be created based on sensor data identified to be of a high-value, measured by sensor 232 and persisting at gateway 310. In such an embodiment, the retrieval API may be capable of filtering through IoT sensor readings transmitted to the gateway 310 from any of the plurality of sensors 230 (including sensor 232), following installation of the retrieval API at the gateway 310. The retrieval API may then filter such future incoming IoT sensor data to identify incoming sensor data meeting the description of high-value sensor data previously received at the gateway 310 from sensor 238. Although the high-value sensor data modeled in the high-value data model 272 originated at sensor 232, the retrieval API in such an embodiment may be capable of quickly identifying similar sensor data as also high-value, even though it originated at sensor 238, based on the fact that the high-value data model 272 describes both the sensor data originating at sensor 232 and sensor data originating at sensor 238. In such a way, the retrieval API may filter through incoming IoT sensor data at gateway 310 to determine which of this incoming IoT sensor data is likely to be of high-value based on past valuation analyses of other sensor data received at gateway 310.

In another example, the retrieval API may be installed at a gateway (not shown) within the enterprise network other than gateway 310. In such an embodiment, the retrieval API may be capable of filtering through IoT sensor readings transmitted to the gateway other than gateway 310 from any of the plurality of sensors in communication with that other gateway. Sensor data originating at one of these plurality of IoT sensors (not shown) in communication with this other gateway in an embodiment may also be described by the high-value data model 272, despite the difference in originating sensors. By identifying such sensor data originating at one of the IoT sensors associated with the gateway other than gateway 310 in an embodiment, the retrieval API operating at this other gateway by determine which of the IoT sensor data incoming to the other gateway is also likely to be of high-value based on past valuation analyses of other sensor data received at gateway 310. In such a way, the high-value data integration system in an embodiment may operate at multiple locations throughout the enterprise network to leverage data valuation scores analyzed at one gateway across several gateways within the enterprise network. In an embodiment in which the high-value data integration system creates a new high-value data model to describe an identified high-value data reading, the method may then end.

Returning to FIG. 5, at block 516, in an embodiment in which a high-value data model already exists to describe the identified high-value data reading, the high-value data integration system operating at least partially at the high-value data model control center may determine whether the high-value data model includes all information available to describe the identified high-value data reading. For example, as described herein, the high-value data model 272 may include all information within the sensor reading and its associated metadata, and may further identify the gateway at which the sensor reading persisted, the firmware in operation at that gateway, whether access restrictions apply to the sensor reading, and the purpose for which the client 280 requested the filtered sensor data 264.

If a high-value data model 272 already exists in an embodiment, the existing high-value data model 272 may have been created to describe a data record other than the data record identified at blocks 504 and 506 as being of high-value. As such, the high-value data model 272 may only partially describe the data record identified at blocks 504 and 506 of being of high value. For example, the data record 274 that is responsive to the API query 262 may have originated from the same type of sensor (e.g., thermostat) as the type of sensor described in the high-value data model 272, but may have originated from a different individual sensor (e.g., thermostat 2) than the individual sensor (e.g., thermostat 1) identified in the high-value data model 272. As another example, the data record 274 that is responsive to the API query 262 may have persisted at the same gateway (e.g., gateway 310) as the gateway identified in the high-value data model 272, but the high-value data model 272 may not describe the version of firmware that was operating at that gateway. As yet another example, the data record 274 that is responsive to the API query 262 may have originated from the same type of sensor (e.g., thermostat) as the type of sensor described in the high-value data model 272, but the high-value data model 272 may not provide a purpose or reason why the data reading it describes was initially identified as being of high-value.

In another example embodiment described with reference to FIG. 4A, one or more of the high-value data models 410, 412, or 414 may describe T1 sensor reading 452, at least in part. However, one or more of the high-value data models 410, 412, or 414 may have been created prior to receipt of T1 sensor reading 452, based on analysis of subscription/queries 402, 404, or 406, respectively. As such, one or more of the high-value data models 410, 412, or 414, determined at block 506 to describe T1 sensor reading 452, may not include all information given in the metadata of T1 sensor reading 452 or otherwise associated with the T1 sensor reading 452 at the gateway 450. For example, one or more of the high-value data models 410, 412, or 414 may not include a valuation score 432 associated with T1 sensor reading 452. If the high-value data model includes all of the information available to describe the high-value data, the method may end. If the high-value data model does not include all of the information available to describe the high-value data, the method may proceed to block 518.

At block 518, the high-value data integration system operating at least partially at the high-value data model control center in an embodiment may add a field to, or otherwise update the high-value data model to reflect the newly available information. For example, in an embodiment in which the data record 274 that is responsive to the API query 262 originated from a different individual sensor (e.g., thermostat 2) than the individual sensor (e.g., thermostat 1) identified in the high-value data model 272, the high-value data model 272 may be updated to also identify the individual sensor that originated the data record 274. As another example, in an embodiment in which the data record 274 that is responsive to the API query 262 does not describe the version of firmware that was operating at that gateway, the high-value data model 272 may be updated to also identify the version of firmware operating at the gateway 310 if that information is available. As yet another example, in an embodiment in which the data record 274 that is responsive to the API query 262 does not provide a purpose or reason why the data reading it describes was initially identified as being of high-value, the high-value data model 274 may be updated to identify the reason (e.g., to identify a malfunctioning IoT sensor) the client 280 requested the API 260 to retrieve the data record 274.

In another example embodiment described with respect to FIG. 4A, one or more of the high-value data models 410, 412, or 414 may be updated to include a valuation score associated with one or more use cases. For example, high-value data model 410 in an embodiment may be updated to include the valuation score of 78% associated with use case 1, high-value data model 412 may be updated to include the valuation score of 96% for use case 3, and high-value data model 414 may be updated to include the valuation score of 27% for use case 2, based on the information given in the valuation score 432, associated with the T1 sensor reading

452. In such a way, the high-value data integration system in an embodiment may identify, and model, the high-value sensor data incoming across a plurality of gateways within an enterprise network.

Figure 6A:
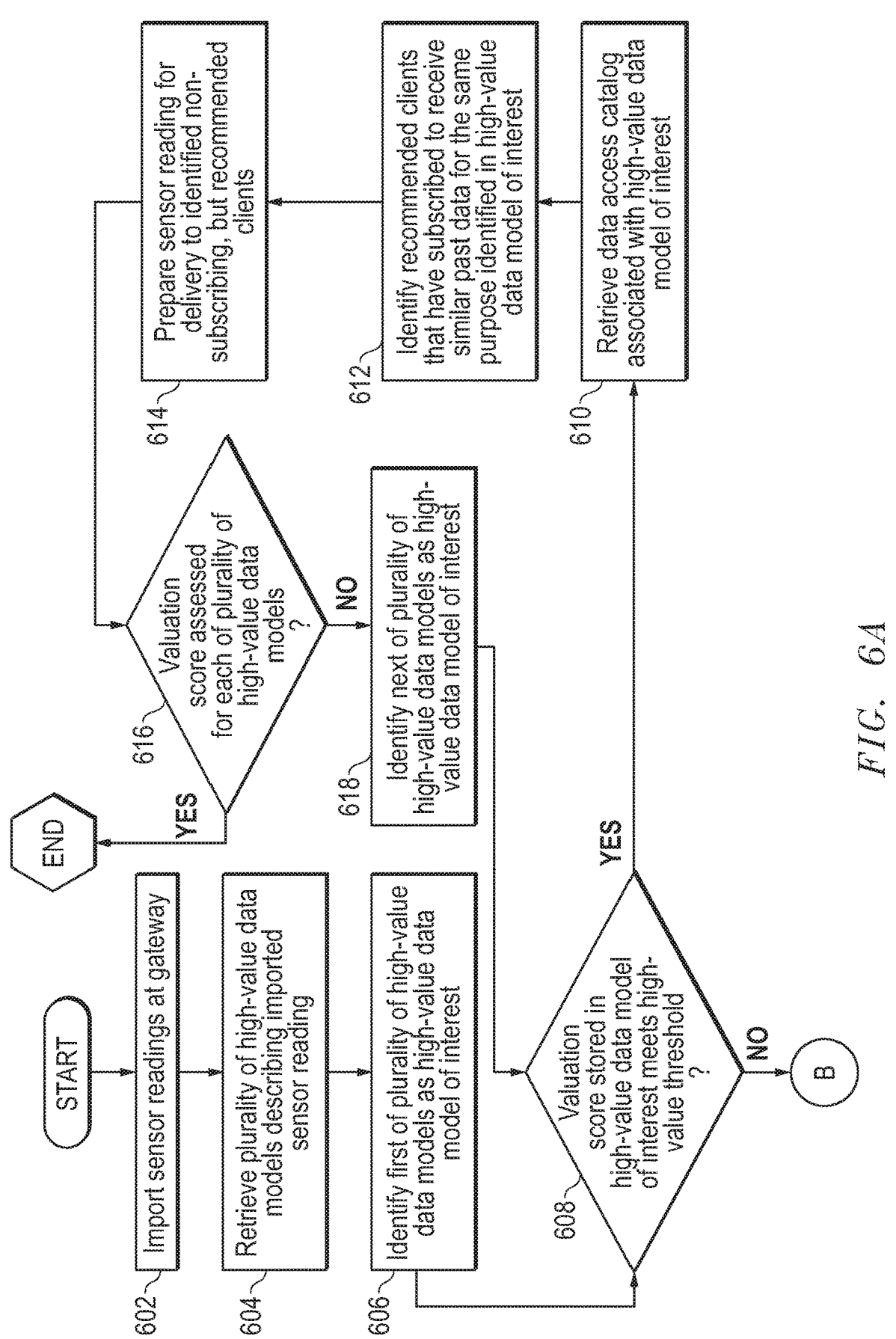
FIG. 6A is a flow diagram illustrating a process of identifying recommended clients who may benefit from receipt of high-value sensor data according to an embodiment of the present disclosure.

FIG. 6A is a flow diagram illustrating a process of identifying recommended clients who may benefit from receipt of high-value sensor data, based on valuation of similar sensor data by subscribing clients according to an embodiment of the present disclosure. As described herein, existing systems do not leverage client valuation of the usefulness of specific types of sensor data to optimize processing and delivery of IoT sensor data to subscribing clients. Such existing systems consequently encounter under-distribution of high-value data. The high-value data integration system described herein addresses this issue, in part, by identifying clients not currently subscribed to receive IoT sensor data likely to be useful to them, and automatically delivering such high-value sensor data to the non-subscribing clients. Identification of recommended clients according to such an approach may be limited to recommending transmission of a given sensor reading to a client that has established security credentials allowing that client access to the given sensor reading. In other words, recommended clients may only include members of the enterprise network having sufficient security credentials to receive and access each sensor reading as it is received.

At block 602, one or more IoT sensor devices in communication with a gateway may transmit a message including a sensor reading and metadata to a gateway device. For example, in an embodiment described with reference to FIG. 2, gateway 210 may operate gateway software 220 to communicate with a plurality of sensors 230, including a variety of sensor types. For example, sensors 232, and 238 may comprise thermostats, sensor 234 may comprise a motor, sensor 236 may comprise a motion detector, sensor 244 may comprise a camera, and sensor 242 may comprise a light sensor (e.g., UV, infrared, or visible light). Each of the plurality of sensors 230 in an embodiment may transmit data to one or more sensors services within the gateway software 220. As another example, in an embodiment described with reference to FIG. 4B, T2 sensor reading 456 may be received at gateway 450.

Returning to FIG. 6A, the retrieval API operating at least in part at the gateway in an embodiment may retrieve a plurality of high-value data models describing, at least in part, the imported sensor reading at block 604. In an embodiment described with respect to FIG. 4B, the retrieval API operating at the gateway 450 may retrieve one or more of high-value data models 412, 414, or 416, which may describe, in part or in whole, information within the T2 sensor reading 456. For example, both T2 sensor reading 456 and the high-value data model 412 may describe a temperature reading from a thermostat sensor operating version 3 of the firmware, and applying an encryption access restriction. As another example, both T2 sensor reading 456 and the high-value data model 414 may describe a humidity reading from a thermostat sensor operating version 3 of the firmware, and applying an encryption access restriction. In yet another example, both T2 sensor reading 456 and the high-value data model 416 may describe a sensor reading from a sensor operating version 3 of the firmware, in communication with gateway 15, and applying an encryption access restriction. In some embodiments, the retrieval API 450 may retrieve each of the high-value data models (e.g., 412, 414, and 416) for temporary storage at the gateway 450.

At block 606, the retrieval API operating at least partially at the gateway in an embodiment may identify a first of the plurality of the high-value data models as a high-value data model of interest. For example, in an embodiment described with reference to FIG. 4B, the retrieval API operating at the gateway 450 may identify the high-value data model 412 as the high-value data model of interest. In another example, the retrieval API may identify high-value data model 414 as the high-value data model of interest. In yet another example, the retrieval API may identify high-value data model 416 as the high-value data model of interest.

The retrieval API operating at least partially at the gateway in an embodiment may determine whether the valuation score associated with the high-value data model of interest meets the high-value threshold at block 608. The high-value threshold in an embodiment may be a preset value, and may depend upon the units used to define the valuation score. For example, in an embodiment in which valuation scores are given as a percentage from zero to 100, the high-value threshold may be 90%. For example, in an embodiment described with reference to FIG. 4B, in which the retrieval API operating at least partially at the gateway 450 has identified the high-value data model 412 as the high-value data model of interest, the retrieval API may determine the valuation score of 96% associated with the high-value data model 412 exceeds the high-value threshold of 90%. As another example, in which the retrieval API identified the high-value data model 414 as the high-value data model of interest, the retrieval API may determine the valuation score of 27% associated with the high-value data model 414 does not meet the high-value threshold of 90%. As yet another example, in which the retrieval API identified the high-value data model 416 as the high-value data model of interest, the retrieval API may determine the valuation score of 78% associated with the high-value data model 416 does not meet the high-value threshold of 90%. If the retrieval API in an embodiment determines the valuation score stored in the high-value data model of interest does not meet the high-value threshold, the method may proceed to FIG. 6B for filtering, and potential distribution to subscribing clients only. If the retrieval API in an embodiment determines the valuation score stored in the high-value data model of interest meets or exceeds the high-value threshold, the method may proceed to block 610 for possible identification of recommended clients that are currently not subscribed to receive the sensor reading imported at block 602, who may benefit from receipt of that sensor reading nonetheless.

At block 610, in an embodiment in which the valuation score associated with the high-value data model of interest meets the high-value threshold, the retrieval API operating at least partially at the gateway may retrieve the data access catalog associated with the high-value data model of interest from a control center. For example, in an embodiment described with reference to FIG. 4B, the high-value data integration system operating at gateway 450 in an embodiment may access a data access catalog 274 to identify clients that are not subscribed to receive sensor reading 456, but who are also likely to benefit from using sensor reading 456 in use cases 1, 2, or 3. As described herein, in an embodiment, a data access catalog 274 may associate a plurality of business units, working groups, use cases, or other logical categorizations with one or more individual clients. For example, the data access catalog 374 may associate business use case 1 with client A, business use case 2 with clients A and C, business use case 3 with clients A, B, C, D, and E, and business use case 4 with clients A, D, and E.

The retrieval API operating at least partially at the gateway in an embodiment may identify one or more recommended clients at block 612. Recommended clients in an embodiment may not be subscribed to receive the sensor reading imported at block 602, but may be subscribed to receive similar past data for the same purpose identified in the high-value data model of interest. For example, in an embodiment described with reference to FIG. 4B, subscribed clients may include only clients A and B, as determined by reference to subscription/queries stored at the export client database, and as reflected in one or more of high-value data models 412, 414, or 416.

The retrieval API in an embodiment may identify recommended clients other than A and B to also receive the T2 sensor reading 456 at block 612. For example, in an embodiment in which the high-value data model 412 is the high-value data model of interest, the retrieval API may identify that the T2 sensor reading 456 has a valuation score of 96% with respect to use case 3. This may indicate a high likelihood that clients not currently subscribed to receive T2 sensor reading 456, but who have used previous sensor readings for the same purpose (e.g., use case 3) may benefit from receipt of T2 sensor reading 456. The retrieval API in such an embodiment may access the data access catalog 274 to identify one or more non-subscribing clients that have used previous sensor data for the same purpose associated with the high-valuation score found in the high-value data model of interest 412. For example, the retrieval API may determine clients C, D, and E, who are not currently subscribed to receive T2 sensor reading 456 in an embodiment have previously consumed sensor readings for business use case 3. This may indicate a likelihood clients C, D, and E may also benefit from receipt of T2 sensor reading 456. In such a way, the retrieval API in an embodiment may improve upon the functionality of the existing EdgeX Foundry™ platform architecture by identifying additional non-subscribing recipients that may benefit from receipt of the sensor reading 454, overcoming the inefficiency of under-publication of high-value data.

At block 614, the high-value data integration system operating at least in part on the gateway may prepare the received sensor reading for delivery to identified recommended clients. For example, in an embodiment described with reference to FIG. 3, the high-valuation subscription 334 may prepare an EdgeX Foundry™ super message for each recommended client. A super message may comprise an aggregation of the sensor reading 320, its metadata, and one or more export client registration records associated with subscribing clients, stored at the export client database 386. In some embodiments, sensor reading 320 may include a plurality of sensor readings 320 from a plurality of IoT sensors or other devices. Further, sensor reading 320 in an embodiment may include a plurality of readings, each measured at different points in time, and may represent a plurality of data points. Super messages for recommended clients 336 in an embodiment may further include an identification of a recommended client, and the high-value data model 372 associated with the sensor reading 320. The high-valuation subscription module 334 may forward the recommended client super messages 336 to the transformation module 348 to prepare the sensor reading 320 for delivery to the identified recommended clients (e.g., including 388). The super messages may be transformed (e.g., compressed, encrypted, etc.), and the publish module 336 may transmit the sensor reading 320, as transformed by the transformation module 334 to the identified recommended clients. In such a way, the high-valuation subscription module 334 in an embodiment may improve upon the functionality of the existing EdgeX Foundry™ platform architecture by identifying additional non-subscribing recipients that may benefit from receipt of the sensor reading 320, overcoming the inefficiency of under-publication of high-value data.

The retrieval API operating at least partially at the gateway in an embodiment may determine at block 616, whether the valuation score has been assessed for each of the plurality of high-value data models. If the valuation scores associated with each high-value data model retrieved at block 604 have not been compared against the high-value threshold, the method may proceed to block 618. If the valuation scores associated with each of the retrieved high-value data models have been compared against the high-value threshold, the retrieval API in an embodiment may have identified each high-value data model for which non-subscribing clients may be appropriately recommended, and the method may end.

At block 618, in an embodiment in which the valuation score has not been assessed for each of the plurality of high-value data models, the retrieval API operating at least partially at the gateway may identify the next of the plurality of high-value data models as a high value data model of interest. The method may then proceed back to block 608 for comparison of the valuation score identified within or associated with the new high-value data model of interest against the high-value threshold. By repeating the loop between block 608 and 618 in such a manner, the retrieval API in an embodiment may identify each high-value data model having a valuation score above a threshold value, then identify one or more clients not subscribed to receive sensor readings described by the high-value data model who may benefit from receipt of such a sensor reading nonetheless. In such a way, the retrieval API in an embodiment may avoid under-publication of high-value sensor readings.

Figure 6B:
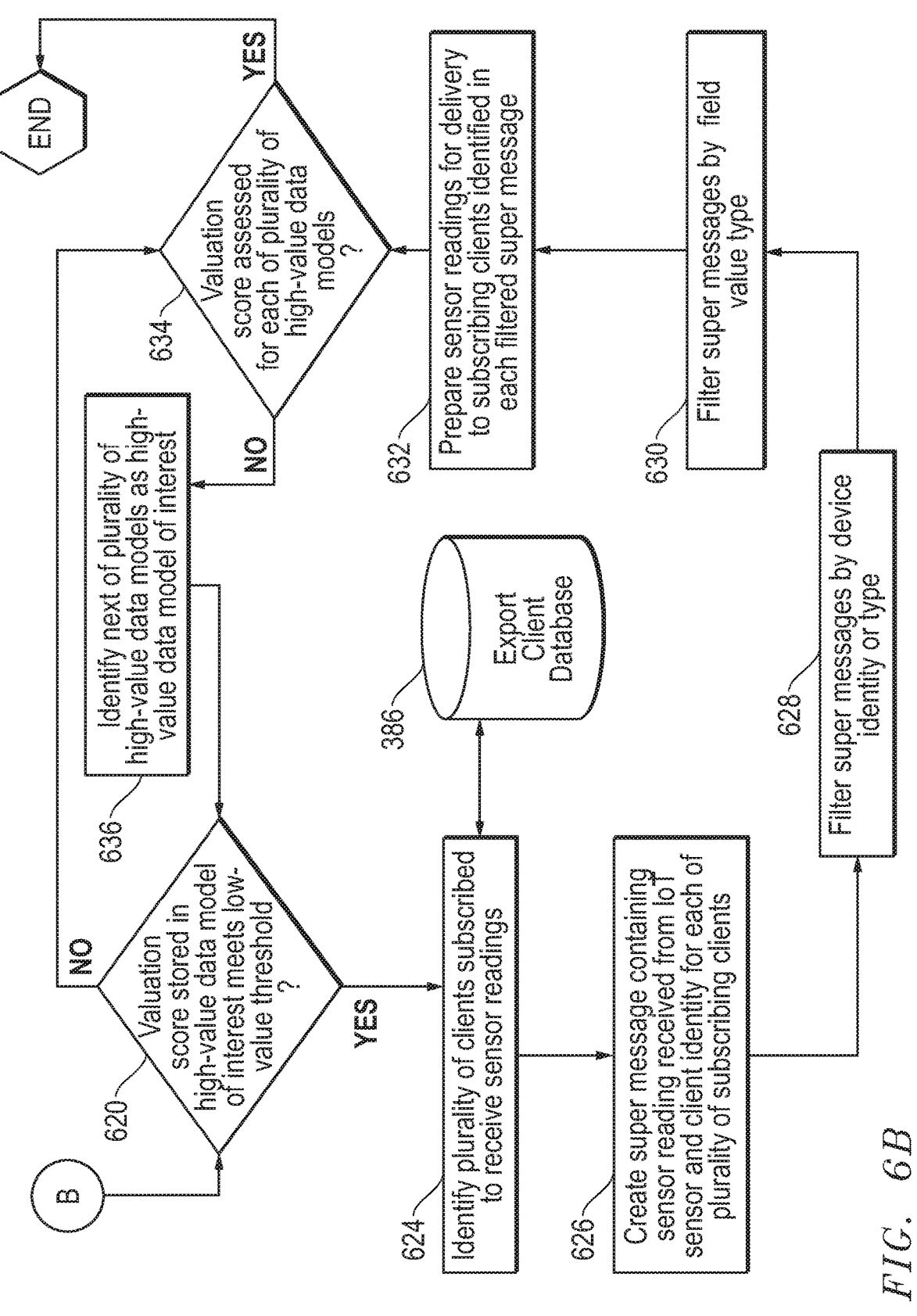
FIG. 6B is a flow diagram illustrating a process of filtering high-value sensor data for delivery to subscribing and recommended clients according to an embodiment of the present disclosure.

FIG. 6B is a flow diagram illustrating a process of filtering high-value sensor data for delivery to subscribing and non-subscribing clients based on a valuation score associated with the sensor data according to an embodiment of the present disclosure. As described with reference to FIG. 6A, if the retrieval API in an embodiment determines the valuation score stored in a high-value data model of interest does not meet the high-value threshold, the method may proceed to FIG. 6B for filtering, and potential distribution to subscribing clients only.

The high-value data model integration system in an embodiment may determine at block 620 whether a valuation score associated with the high-valuation data model of interest meets a minimum threshold value in an embodiment. The minimum threshold value in an embodiment may define a minimum level of usefulness to subscribing clients to justify the processing and electronic transportation overhead associated with transforming and publishing such data. For example, if a client is subscribed to receive a set of sensor readings, but upon later inspection, it is determined the client never actually uses such a set of sensor readings, it may also be determined the overhead associated with transformation and publication of that set of sensor readings is not justified.

The minimum threshold value in an embodiment may be preset and have a lower value than the high-value threshold. For example, the minimum threshold value may be 30% in an embodiment in which the high-value threshold is 90%. These are only example values, and other embodiments may set high-value threshold and minimum threshold to have any values corresponding with the units in which valuation scores associated with high-value data models and incoming sensor readings are kept.

In an embodiment in which the valuation score stored in the high-value data model of interest meets or exceeds the low-value or minimum threshold, the method may proceed to block 624. For example, in an embodiment described with reference to FIG. 4B in which the high-value data model 416 is the high-value data model of interest, the retrieval API may determine the valuation score of 78% exceeds a low-value or minimum threshold value of 30%. In an embodiment in which the valuation score stored in the high-value data model of interest does not meet the low-value or minimum threshold, the method may proceed to block 634. For example, in an embodiment described with reference to FIG. 4B in which the high-value data model 414 is the high-value data model of interest, the retrieval API may determine the valuation score of 27% does not meet a low-value or minimum threshold value of 30%. The retrieval API in such an embodiment may not prepare the sensor reading for delivery to clients identified as subscribers within the high-value data model 414 having a valuation score of 27%. In such an embodiment, the retrieval API may move on to analyze the next high-value data model of interest associated with the received sensor reading. In such a way, the retrieval API in an embodiment may avoid unnecessary expenditure of overhead on low-value sensor readings.

At block 624, in an embodiment in which the valuation score stored in the high-value data model of interest meets a low-value minimum threshold, the retrieval API may identify a plurality of clients subscribed to receive the sensor reading imported at block 602. The high-value data integration system operating, at least in part, on the gateway in an embodiment may request and receive client subscriptions stored at the export client database 386 to determine a plurality of clients subscribed to receive sensor data matching the description of the sensor reading received at block 602. For example, in an embodiment described with reference to FIG. 3, a client copier 340 operating at the gateway 310 may access a plurality of client subscription registration records stored at the export client database 386 in order to identify client 380 subscribing to receive temperature readings recorded by a thermostat, in communication with gateway 310, operating version 3 of the firmware. If sensor reading 320 meets any one of these descriptions, the client copier 340 in an embodiment may identify client 380 as having subscribed to receive sensor reading 320. While client 380 has actually subscribed to receive sensor readings that match each of the descriptors provided in the client registration subscription record, rather than only one, the client copier 340 may still identify client 380 as having subscribed to receive sensor reading 320. This may be the case because the sensor reading 320 may pass through several filters after the client copier 340 designates client 380 as a subscribing client. Each of these filters may operate to ensure client 380 only receives sensor readings meeting each of the descriptors, rather than only one descriptor.

The high-value data integration system operating at least in part on the gateway in an embodiment may create a plurality of super messages containing the sensor reading received from the IoT sensor and the subscription information for the plurality of identified subscribing clients at block 626. For example, the client copier 340 in an embodiment may create a plurality of "super messages," each including the sensor reading 320, and one client subscription registration record associated with each of the identified subscribing clients (e.g., client 380). The field values within the client subscription registration record may be used to filter data toward specific subscribing clients, including client 380 in an embodiment.

At block 628, the high-value data integration system in an embodiment may filter the content of the plurality of super messages of interest based on an identification of IoT sensors to which the client identified in super message is subscribed. For example, the client registration subscription record may identify gateway 310 in the gateway ID field, but may further identify thermostat sensors in the device type field. The client may then be considered to be subscribed to all sensor readings imported to gateway 310. The device filter module 342 in an embodiment may discard super messages unless the sensor device that originated the sensor reading 320 is described in the sensor type field in the client registration subscription record within the super message. For example, the device filter module 342 may discard the super message in such an embodiment if the client registration subscription record identifies thermostat sensors in communication with gateway 310, but the sensor reading 320 was recorded by a camera sensor in communication with gateway 310, rather than a thermostat sensor. In such a way, the retrieval API 330 may narrow the number of super messages requiring further processing.

In another embodiment, the high-value data integration system in an embodiment may discard the super message of interest unless the client is subscribed to the individual IoT sensor originating the data reading within the super message of interest. For example, a client may be identified as having subscribed to receive a sensor reading 320 constituting a temperature measurement and a humidity measurement from a thermostat sensor in communication with gateway 310, executing firmware version 3.0, if the client's registration subscription record identifies sensor readings from a thermostat sensor. However, the client's registration subscription record may also provide other descriptors that can be used to narrow the breadth of data the client is interested in receiving. For example, the client's registration subscription record may identify thermostat sensors in the sensor type field, but may further identify a specific thermostat in communication with gateway 310, executing firmware version 3.0 in other fields. The device filter module 330 in an embodiment may discard super messages unless the sensor device that originated the sensor reading 320 is described in the sensor identification field in the client registration subscription record within the super message. For example, the device filter module 330 may discard a super message containing sensor reading 320 if it originated from the second thermostat sensor in communication with gateway 310, but the client registration subscription record only identifies the first thermostat sensor in communication with gateway 310. In such a way, the retrieval API 330 may narrow the number of super messages requiring further processing.

At block 630 in an embodiment, the high-value data integration system may filter content of the super message of interest based on the type of readings measured by the IoT sensor to which the client identified in the super message is subscribed. For example, the client in an embodiment may have only subscribed to receive certain types of sensor readings measured at a given device or type of device. In such an embodiment, the client registration subscription record may identify temperature measurements originating at a thermostat sensor in communication with gateway 310, but not humidity measurements. The field value filter module 344 in an embodiment may discard fields within a super message if the client registration subscription record within the super message only identifies a subset of field values given in the sensor reading 320. For example, the sensor reading 320 in an embodiment may include both humidity and temperature measurements from a thermostat sensor in communication with gateway 310. In such an embodiment, if the client registration subscription record only identifies the client's interest in temperature readings from thermostat sensors in communication with the gateway 310, the field value filter 344 may remove the humidity measurement from the super message.

The high-value data integration system in an embodiment may prepare the filtered super message of interest for delivery to the associated subscribing client at block 632. For example, the field value filter module 344 in an embodiment may transmit the super messages, each containing the sensor reading 320 and a client registration subscription record to the transformation module 348. The filtered super messages may be transformed (e.g., compressed, encrypted, etc.) before being sent to each of the registered clients, including client 380 via the publication module 350. In some embodiments, the transformation module 348 may perform encryption or other access restriction methods to ensure access to the sensor reading 320 included within the super message is restricted in accordance with the access restrictions identified in the metadata for the sensor reading 320, also included in the super message. For example, access may be restricted based on the route through which the sensor reading 320 will be published to the client (e.g., based on identification of IP or MAC addresses, IP ranges, URLs of nodes through which the sensor reading 320 passes to reach the client 380). As another example, access may be restricted based on the time of publication. The publish module 350 in an embodiment may identify the subscribing client for each received super message, and may transmit the sensor reading 320, as transformed by the transformation module 348 to the identified subscribing client. In such a way, the high-value data integration system in an embodiment may overcome the inefficiency of over-publication of low-value data associated with existing EdgeX Foundry™ platform architectures.

At block 634, the high-value data integration system in an embodiment may determine whether the valuation scores for each of the plurality of high-value data models have been compared against the low-value or minimum threshold value. If the valuation scores associated with each high-value data models retrieved at block 604 have not been compared against the low-value or minimum threshold, the method may proceed to block 636. If the valuation scores associated with each of the retrieved high-value data models have been compared against the low-value or minimum threshold, the retrieval API in an embodiment may have filtered out each inefficient use of the sensor reading received at block 602, avoiding unnecessary over-publication of low-value sensor readings, and the method may end.

In an embodiment in which the valuation score for each of the plurality of high-value data models has not been compared against the low-value or minimum threshold, the retrieval API operating at least partially at the gateway may identify the next of the plurality of high-value data models as a high value data model of interest of block 636. The method may then proceed back to block 620 for comparison of the valuation score identified within or associated with the new high-value data model of interest against the low-value or minimum threshold. By repeating the loop between block 620 and 636 in such a manner, the retrieval API in an embodiment may avoid over-publication of low-value sensor readings.

The blocks of the flow diagrams (FIGS. 5, 6A, and 6B) discussed above need not be performed in any given or specified order. It is contemplated that additional blocks, steps, or functions may be added, some blocks, steps or functions may not be performed, blocks, steps, or functions may occur contemporaneously, and blocks, steps or functions from one flow diagram may be performed within another flow diagram. Further, those of skill will understand that additional blocks or steps, or alternative blocks or steps may occur within the flow diagrams discussed for the algorithms above.

Although only a few exemplary embodiments have been described in detail herein, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

The above-disclosed subject matter is to be considered illustrative, and not restrictive, and the appended claims are intended to cover any and all such modifications, enhancements, and other embodiments that fall within the scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An information handling system of a gateway computing node operating a high-value data integration system comprising:

the gateway computing node operably and communicatively coupled to an enterprise network having a hardware processor executing computer readable code instructions of a high-value data model data control center for an enterprise that receives a plurality of Internet of Things (IoT) sensor data readings from a plurality of IoT sensors and operatively coupled to store the plurality of IoT sensor data readings in a sensor data lake storage;

the gateway computing node having a gateway network interface device to receive, from the high-value data model data control center, executable computer readable code instructions of a high-value data model algorithm included with an automatically-generated retrieval application programming interface (API) generated by the high-value data model data control center;

the hardware processor at the gateway computing node executing computer readable code instructions of the high-value data model algorithm using the automatically-generated retrieval API to filter IoT sensor data in a data lake stored from the plurality of remotely-located IoT sensors for a subscribing recipient based on determination of a valuation score for IoT sensor data attributed to the subscribing recipient as representing high-value IoT sensor data, where the valuation score represents a usefulness percentage determined from tracking a level data mining queries and use of resulting received IoT sensor data from the data lake by the subscribing recipient in applications from a first client information handling system of the subscribing recipient;

the gateway computing node to store in memory the valuation score determined for IoT sensor data in metadata for IoT sensor data from corresponding IoT sensors and for IoT sensors of a similar IoT device type in the enterprise at the sensor data lake storage;

the hardware processor of the gateway computing node to execute code instructions of the automatically-generated retrieval API to filter the IoT sensor data received from the plurality of IoT sensors of an IoT device type located at plural locations within an enterprise for the subscribing recipient by using a model field value matching a metadata descriptor associated with at least one IoT sensor data reading that matches the valuation score associated with high-value IoT sensor data for the subscribing recipient at the first client information handling system while not accessing IoT sensor data readings in the sensor data lake storage that do not match the valuation score associated with and determined for high-value IoT sensor data for the subscribing recipient; and the gateway computing node to transmit at least one sensor reading of the IoT sensor data from corresponding IoT sensors and for IoT sensors of the similar IoT device type in the enterprise for the enterprise to the first client information handling system of the subscribing recipient.

2. The information handling system operating the high-value data integration system of claim 1 further comprising:

the hardware processor to identify a subsequent client information handling system as a subscribing recipient where of the gateway computing node based on a client subscription record received from a remote export client database for a subsequent subscribing recipient; and the gateway network interface device to transmit the at least one sensor reading to the subsequent client information handling system of the subsequent subscribing recipient if the valuation score for the at least one sensor reading of a first IoT sensor among the plurality of IoT sensors within the high-value data model meets a low-value data score threshold value.

3. The information handling system operating the high-value data integration system of claim 1, wherein the valuation score is determined based on the use of resulting received IoT sensor data in the applications from the first client information handling system tracked for the subscribing recipient as monitored by the high-value data model data control center for the enterprise to improve accuracy of a determination of a probability level that the first client information handling system consumes the at least one IoT sensor data reading from the IoT sensor relative to the other IoT sensor data of the plurality of IoT sensors stored in the sensor data lake storage.

4. The information handling system operating the high-value data integration system of claim 1, wherein the automatically-generated retrieval API filters the IoT sensor data received from the plurality of IoT sensor devices between a first IoT sensor and a second IoT sensor, both within the plurality of IoT sensors, to IoT data sensor readings upon which the second IoT sensor may act when the second IoT sensor depends on data from the first IoT sensor so sensor data from both the first IoT sensor and the second IoT sensor are not reported to the subscribing recipient.

5. The information handling system operating the high-value data integration system of claim 1, wherein the automatically-generated retrieval API filters the IoT sensor data received from the plurality of IoT sensor devices based on determination of the probability level that the first client information handling system uses the IoT sensor data from a first IoT sensor relative to the other IoT sensor data of the plurality of IoT sensors based on data identifying the subscribing recipient performing maintenance upon, or repairing a defective one of the plurality of IoT sensors communicatively coupled to the gateway computing node.

6. The information handling system operating the high-value data integration system of claim 1, wherein the automatically-generated retrieval API filters the IoT sensor data received from the plurality of IoT sensor devices based on determination of the probability level of the first client information handling system using the IoT sensor data from a first IoT sensor relative to the other IoT sensor data of the plurality of IoT sensors based on data describing monitored usages of the at least one IoT sensor data reading from the first IoT sensor by a specifically identified application executing on the first client information handling system by the subscribing recipient.

7. The information handling system operating the high-value data integration system of claim 1 further comprising:

the executable computer readable code instructions of the high-value data model includes an access restriction requirement; and the hardware processor to transform the at least one sensor reading to comply with the access restriction requirement prior to publication of the at least one sensor reading to the subscribing recipient at the first client information handling system.

8. A method of automatically customizing a sensor data integration, comprising:

receiving, via a gateway network interface device, a sensor reading at a gateway computing node from a first Internet of Things (IoT) sensor of a plurality of IoT sensors located at different locations within an enterprise facility and communicatively coupled to the gateway computing node of an enterprise network and the gateway computing node storing sensor data from the plurality of IoT sensors in a sensor data lake storage;

executing, via a hardware processor at the gateway computing node, for use with executable computer readable code instructions of an automatically generated retrieval application programming interface (API) having a high-value data model algorithm received from a remote high-value data model data control center server in the enterprise to filter and sort IoT sensor data stored in a data lake from the plurality of IoT sensors at the gateway computing node using the automatically-generated retrieval API for a subscribing recipient based on a determination of a valuation score for the IoT sensor data attributed to the subscribing recipient as representing high-value IoT sensor data for the subscribing recipient, where the valuation score is a usefulness percentage determined from tracking data for levels of mining queries and use of resulting received IoT sensor data from the data lake by the subscribing recipient in applications from a first client information handling system of the subscribing recipient and tracked by the remote high-value data model data control center server in the enterprise;

executing computer readable code instructions of the automatically generated retrieval API with the high value data model algorithm to include a model field value matching a metadata descriptor associated with the sensor reading and the valuation score determined for the determination of high-value sensor data for the subscribing recipient at the first client information handling system representing a determined probability level that the first client information handling system uses a first type of IoT sensor data from the first IoT sensor that is greater than other IoT sensor data of other IoT sensors of the plurality of IT sensors when the valuation score meets a high-value data valuation score threshold for the subscribing recipient and other sensor data from the plurality of IoT sensors that does not meet the high-value data valuation score threshold for a high-value sensor data criteria under the high-value data model of the automatically generated retrieval API; and transmitting, via the gateway network interface device, the first type of IoT sensor data of the first IoT sensor to the recommended subscribing recipient at the first client information handling system from the gateway computing node without a data mining query.

9. The method of claim 8, wherein the computer readable code instructions of the automatically generated retrieval API with the high value data model algorithm identifies a class of IoT sensors to which the first IoT sensor of a plurality of IoT sensors belongs.

10. The method of claim 8, wherein the computer readable code instructions of the automatically generated retrieval API with the high value data model algorithm identifies the gateway computing node and a plurality of IoT sensor data types.

11. The method of claim 8, wherein the computer readable code instructions of the automatically generated retrieval API with the high value data model algorithm represents a determination of probability levels for the types of IoT sensor data from the plurality IoT sensors including the first type of IoT sensor data from the first IoT sensor associated with the first client information handling system being used by the subscribing recipient at the first client information handling systems based on data identifying, performing maintenance upon, or repairing a defective one of the plurality of IoT sensors.

12. The method of claim 8, wherein the computer readable code instructions of the automatically generated retrieval API with high-value data model includes an access restriction requirement further comprising transforming the at least one sensor reading of the first type of IoT data of the first IoT sensor, via the processor, to comply with the access restriction requirement prior to publication of the at least one sensor reading to the recommended subscribing recipient at the first client information handling system.

13. The method of claim 12, wherein the access restriction requirement is a method of encryption.

14. The method of claim 12, wherein the access restriction requirement includes requiring a valid username and a password.

15. An information handling system of a gateway computing node operating a high-value data integration system comprising:

the gateway computing node operably and communicatively coupled, via a gateway network interface device, to an enterprise network executing a high-value data model data control center within the enterprise network;

the gateway computing node communicatively coupled to receive, via the gateway network interface device, a plurality of sensor readings from a first Internet of Things (IoT) sensor and a plurality of IoT sensors and communicatively coupled to a sensor data lake storage to store the plurality of sensor readings;

the gateway computing node to receive, via the gateway network interface device, from the high-value data model data control center within the enterprise network, computer readable code instructions of an automatically generated retrieval application programming interface (API) with a high-value data model algorithm to filter IoT sensor data from the plurality of IoT sensors stored in a data lake operatively coupled to the gateway computing node for a subscribing recipient at a first client information handling system based on a valuation score determined for the sensor data attributed to the subscribing recipient a representing high-value IoT sensor data, where the valuation score is determined based on a relevance level to the subscribing recipient determined from taxonomy mapping to keywords tracked as used by a subscribing user operating a first client information handling system to retrieve IoT sensor data from the data lake;

a hardware processor at the gateway computing node executing the computer readable code instructions of the automatically generated retrieval API with the high value data model algorithm to determine a model field value matching one of a plurality of metadata descriptors associated with the sensor reading that meets the valuation score determined for the determination of high-value sensor data meeting a high-value data valuation score threshold for the subscribing recipient to represent a probability level that a first type of sensor reading from a first IoT sensor is used by subscribing recipient at the first client information handling system relative to the plurality of additional types of sensor readings from the plurality of other IoT sensors; and the gateway network interface device at the gateway computing node to transmit the sensor reading to the subscribing recipient at the first client information handling system when the valuation score for the first type of sensor reading from the first IoT sensor meets the high-value data valuation score threshold for the subscribing recipient.

16. The information handling system of 15, wherein a data model descriptor in the automatically generated retrieval API with the high value data model identifies a specific IoT sensor device for the first IoT sensor.

17. The information handling system of claim 15, wherein the computer readable code instructions of the automatically generated retrieval API with the high value data model algorithm identifies a specific type of sensor reading type for the first type of IoT sensor device.

18. The information handling system of claim 15, wherein the computer readable code instructions of the automatically generated retrieval API with the high value data model algorithm identifies a version of firmware operating on one or more of the plurality of IoT sensors.

19. The information handling system of claim 15 further comprising:

the computer readable code instructions of the automatically generated retrieval API with the high-value data model includes an access restriction requirement; and the hardware processor to transform the first type of sensor reading and the additional types of sensor readings to comply with the access restriction requirement prior to publication of the first type of sensor reading and the additional types of sensor readings to the subscribing recipient client information handling system.

20. The information handling system of claim 19, wherein the access restriction requirement includes allowing access based on a media access control (MAC) address of the gateway computing node.

\* \* \* \* \*